US008084609B2

(12) United States Patent
Bissantz et al.

(10) Patent No.: US 8,084,609 B2
(45) Date of Patent: *Dec. 27, 2011

(54) SPIROPIPERIDINE DERIVATIVES

(75) Inventors: Caterina Bissantz, Village Neuf (FR); Christophe Grundschober, Rodersdorf (CH); Raffaello Masciadri, Basel (CH); Hasane Ratni, Habsheim (FR); Mark Rogers-Evans, Oberwil (CH); Patrick Schnider, Bottmingen (CH)

(73) Assignee: Hoffman-La Roche Inc., Nutley, NJ (US)

( * ) Notice: Subject to any disclaimer, the term of this patent is extended or adjusted under 35 U.S.C. 154(b) by 944 days.

This patent is subject to a terminal disclaimer.

(21) Appl. No.: 11/955,452

(22) Filed: Dec. 13, 2007

(65) Prior Publication Data

US 2008/0153861 A1    Jun. 26, 2008

(30) Foreign Application Priority Data

Dec. 22, 2006   (EP) .................................. 06127086

(51) Int. Cl.
*C07D 405/04*    (2006.01)
*A61K 31/438*    (2006.01)
(52) U.S. Cl. .............................. 546/17; 546/18; 514/279
(58) Field of Classification Search .................... 546/18; 514/279
See application file for complete search history.

(56) References Cited

U.S. PATENT DOCUMENTS

| 3,370,091 | A | 2/1968 | Archer et al. |
| 3,531,467 | A | 9/1970 | Archer et al. |
| 4,209,625 | A | 6/1980 | Ong et al. |
| 5,019,587 | A | 5/1991 | Von Der Saal et al. |
| 5,670,509 | A | 9/1997 | Evans et al. |
| 5,885,999 | A | 3/1999 | Elliott et al. |
| 7,332,501 | B2 | 2/2008 | Bissantz et al. |
| 7,498,339 | B2 | 3/2009 | Bissantz et al. |
| 2001/0039286 | A1 | 11/2001 | Dinnell et al. |
| 2002/0052371 | A1 | 5/2002 | Fukami et al. |
| 2004/0260100 | A1 | 12/2004 | Ku et al. |
| 2008/0139554 | A1 | 6/2008 | Bissantz et al. |
| 2008/0153863 | A1 | 6/2008 | Bissantz et al. |
| 2008/0171760 | A1 | 7/2008 | Bissantz et al. |
| 2008/0281103 | A1 | 11/2008 | Bissantz et al. |

FOREIGN PATENT DOCUMENTS

| EP | 344634 | 12/1989 |
| EP | 0718280 | 6/1996 |
| EP | 722941 | 7/1996 |
| EP | 2019093 | 1/2009 |
| WO | 93/25527 | 12/1993 |
| WO | WO 94/07496 | 4/1994 |
| WO | WO 97/21704 | 6/1997 |
| WO | WO 99/29696 | 6/1999 |
| WO | 00/14067 | 3/2000 |
| WO | 00/25780 | 5/2000 |
| WO | 00/78731 | 12/2000 |
| WO | WO 01/14376 | 3/2001 |
| WO | 01/85725 | 11/2001 |
| WO | WO 02/28861 | 4/2002 |
| WO | 03/040141 | 5/2003 |
| WO | WO 03/045385 | 6/2003 |
| WO | WO 03/053939 | 7/2003 |
| WO | 2004/022528 | 3/2004 |
| WO | 2004/026855 | 4/2004 |
| WO | 2004/035549 | 4/2004 |
| WO | 2004/046118 | 6/2004 |
| WO | 2004/069809 | 8/2004 |
| WO | 2004/087699 | 10/2004 |
| WO | 2004/089470 | 10/2004 |
| WO | 2005/013996 | 2/2005 |
| WO | 2005/046682 | 5/2005 |
| WO | WO 2005/063745 | 7/2005 |
| WO | WO 2006/013048 | 2/2006 |
| WO | WO 2006/040329 | 4/2006 |

(Continued)

OTHER PUBLICATIONS

Evans, B et al, *Jour. Of Med. Chem.*, 35:(21) (1992) 3919-3927.
Ebner et al., Eur. J. Neurosci. vol. 15, pp. 384-388 (2002).
Bielsky et al., Neuropsychopharmacology vol. 29, pp. 483-493 (2004).
Michelini et al., Ann. NY Acad. Sci. vol. 897 pp. 198-211 (1999).
Vankerckhoven et al., Eur. J. Pharmacol. vol. 449, Issue 1-2, pp. 135-141 (2002).
Liebsch et al., Regulatory Peptides vol. 59, Issue 2, pp. 229-239 (1995).
Parham et al., J. Org. Chem. vol. 41, pp. 2628-2633 (1976).
Moltzen et al., J. of Medicinal Chemistry vol. 38(11) pp. 2009-2017 (1995).

(Continued)

*Primary Examiner* — Rita Desai
(74) *Attorney, Agent, or Firm* — George W. Johnston; Patricia S. Rocha-Tramaloni; Kimberly J. Prior

(57) ABSTRACT

The present invention is concerned with novel spiro-piperidine derivatives as V1a receptor antagonists, their manufacture, pharmaceutical compositions containing them and their use for the treatment of anxiety and depressive disorders and other diseases. The compounds of present invention are described with formula (I)

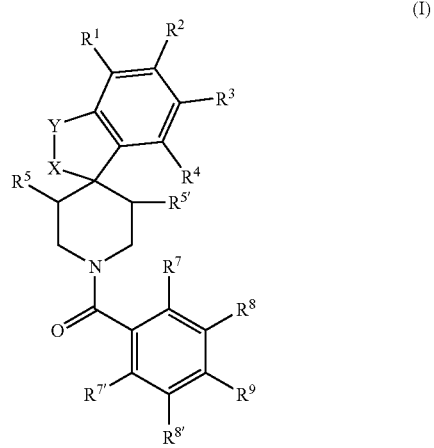

(I)

wherein $R^1$ to $R^5$, $R^{5'}$, $R^7$ to $R^9$, $R^{7'}$, $R^{8'}$, X and Y are as defined in the specification.

26 Claims, No Drawings

FOREIGN PATENT DOCUMENTS

| WO | WO 2006/123242 | 11/2006 |
|---|---|---|
| WO | WO 2007/028638 | 3/2007 |
| WO | 2007/053452 | 5/2007 |
| WO | 2008/006103 | 1/2008 |
| WO | 2008/138753 | 11/2008 |
| WO | 2009/032861 | 3/2009 |

OTHER PUBLICATIONS

Serradeil-Le-Gal et at, Elsevier vol. 139, 2002, pp. 197-210 XP001205440.
Elliott et al., Serine derived NK1 antagonists 1998, Bioorganic & Medicinal Chem. Letters, vol. 8, pp. 1851-1856.
Abdel-Magid et al., J. Org. Chem, 1996, vol. 61 pp. 3849-3862.
Mattson et al,. J. Org. Chem. vol. 55, 1990, pp. 2552-2554.
Lecointe et al., Journal of Peptide Research vol. 55, 2000 pp. 300-307.
Baeza et al., Synthesis 2005, pp. 2787-2797.
Deuchert et al., Chem. Ber. vol. 112, 1979 pp. 2045-2061.
Dejaegher et al., Synlett 2002 pp. 113-115.
Grisar et al., J. Med. Chem. vol. 16, 1973 pp. 885-893.
Brenner et al., J. Heterocyclic Chem. vol. 22, 1985 pp. 805-808.
Sasse et al., Bioorganic & Medicinal Chem. vol. 8, 2000 pp. 1139-1149.
Terrasson et al., Synthesis 2006 pp. 1858-1862.
Fryer et al., J. Heterocyclic Chem vol. 4, 1967 pp. 149-150.
Walker et al., J. Org. Chem. vol. 36, 1970 pp. 305-308.
Walser et al., J. Heterocyclic Chem. vol. 11, 1974 pp. 885-888.
Fryer et al., J. Heterocyclic Chem. vol. 14, 1977, pp. 1435-1437.
Clerici et al., J. Org. Chem. vol. 47, 1982 pp. 2852-2856.
Clerici et al., J. Org. Chem. vol. 58, 1993, pp. 2889-2893.
Pfoertner et al., Helv. Chim. Acta vol. 68, 1985 pp. 600-605.
Xiang et al., Bioorganic & Med. Chem. Letters, 2004, pp. 2987-2989 XP004841329.
Delgado et al., J. Org. Chem. vol. 10, 1993, pp. 2862-2866.
Dorwald, F. A., Side Reactions in Organic Synthesis, 2005 pp. 8-9.
Genin et al., Design & Synthesis of BHAP, 1995, pp. 1875-1880.
Office Action Issued Mar. 8, 2011—in corresponding U.S. Appl. No. 11/964,993, filed Jan. 7, 2008.
Office Action Issued Feb. 14, 2011—in corresponding U.S. Appl. No. 11/969,983, filed Jan. 7, 2008.
Office Action Issued Feb. 1, 2011—in corresponding U.S. Appl. No. 11/960,823, filed Dec. 20, 2007.
Office Action Issued Feb. 1, 2011—in corresponding U.S. Appl. No. 11/960,799, filed Dec. 20, 2007.
Office Action Issued Jan. 19, 2011—in corresponding U.S. Appl. No. 11/947,953, filed Nov. 30, 2007.
Office Action Issued Feb. 2, 2011—in corresponding U.S. Appl. No. 11/960,779, filed Dec. 20, 2007.
Office Action Issued Jan. 21, 2011—in corresponding U.S. Appl. No. 11/947,967, filed Nov. 30, 2007.
Office Action Issued Jan. 20, 2011—in corresponding U.S. Appl. No. 11/947,934, filed Nov. 30, 2007.
Alfaidy et al., J. Clin. Invest. vol. 100, No. 10 pp. 2437-2442 (1997).
Office Action Issued Jan. 19, 2011—in corresponding U.S. Appl. No. 11/955,466, filed Dec. 13, 2007.
Office Action Issued Jan. 20, 2011—in corresponding U.S. Appl. No. 11/955,460, filed Dec. 13, 2007.
English Translation of Korean Office Action, 1992.
(Translation of Chinese Office Action in Corres. Pat. Appl. 200780046736.0 May 11, 2011).
Dhar et al., Bioorganic & Medicinal Chemistry Letters (XP002522864), 12(12):3125-3128 ( 2002).
Paul et al., Jour. of Medicinal Chemistry (XP002522865), 36(19):2716-2725 ( 1999).

SPIROPIPERIDINE DERIVATIVES

PRIORITY TO RELATED APPLICATION(S)

This application claims the benefit of European Patent Application No. 06127086.4, filed Dec. 22, 2006, which is hereby incorporated by reference in its entirety.

BACKGROUND OF THE INVENTION

Vasopressin is a 9 amino acid peptide mainly produced by the paraventricular nucleus of the hypothalamus. Three vasopressin receptors, all belonging to the class I G-protein coupled receptors, are known. The V1a receptor is expressed in the brain, liver, vascular smooth muscle, lung, uterus and testis, the V1b or V3 receptor is expressed in the brain and pituitary gland, the V2 receptor is expressed in the kidney where it regulates water excretion and mediates the antidiuretic effects of vasopressin.

In the periphery vasopressin acts as a neurohormone and stimulates vasoconstriction, glycogenolysis and antidiuresis. In the brain vasopressin acts as a neuromodulator and is elevated in the amygdala during stress (Ebner, K., C. T. Wotjak, et al. (2002). "Forced swimming triggers vasopressin release within the amygdala to modulate stress-coping strategies in rats." Eur J Neurosci 15(2): 384-8). The V1a receptor is extensively expressed in the brain and particularly in limbic areas like the amygdala, lateral septum and hippocampus which are playing an important role in the regulation of anxiety. Indeed V1a knock-out mouse show a reduction in anxious behavior in the plus-maze, open field and light-dark box (Bielsky, I. F., S. B. Hu, et al. (2003). "Profound Impairment in Social Recognition and Reduction in Anxiety-Like Behavior in Vasopressin V1a Receptor Knockout Mice." Neuropsychopharmacology). The downregulation of the V1a receptor using antisense oligonucleotide injection in the septum also causes a reduction in anxious behavior (Landgraf, R., R. Gerstberger, et al. (1995). "V1 vasopressin receptor antisense oligodeoxynucleotide into septum reduces vasopressin binding, social discrimination abilities, and anxiety-related behavior in rats." Regul Pept 59(2): 229-39).

The V1a receptor is also mediating the cardiovascular effects of vasopressin in the brain by centrally regulating blood pressure and heart rate in the solitary tract nucleus (Michelini, L. C. and M. Morris (1999). "Endogenous vasopressin modulates the cardiovascular responses to exercise." Ann NY Acad Sci 897: 198-211). In the periphery it induces the contraction of vascular smooth muscles and chronic inhibition of the V1a receptor improves hemodynamic parameters in myocardial infarcted rats (Van Kerckhoven, R., I. Lankhuizen, et al. (2002). "Chronic vasopressin V(1A) but not V(2) receptor antagonism prevents heart failure in chronically infarcted rats." Eur J Pharmacol 449(1-2): 135-41).

SUMMARY OF THE INVENTION

The present invention provides novel spiro-piperidine derivatives as V1a receptor antagonists, their manufacture, pharmaceutical compositions containing them and their use for the treatment of anxiety and depressive disorders and other diseases.

In particular, the present invention provides compounds of formula (I)

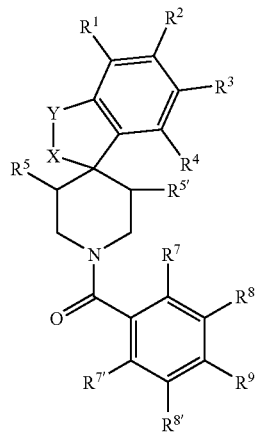

(I)

wherein
 X is O and Y is C=O,
 X is O and Y is $CH_2$,
 X is C=O and Y is $NR^6$,
 X is $CH_2$ and Y is O,
 X—Y is CH=CH,
 X—Y is $CH_2$—$CH_2$,
 X is C=O and Y is O, or
 X is $CH_2$ and Y is $NR^6$;
$R^1$, $R^2$, $R^3$ and $R^4$ are each independently
 hydrogen,
 halo,
 $C_{1-6}$-alkyl, optionally substituted by OH,
 halo-$C_{1-6}$-alkyl,
 $C_{1-6}$-alkoxy, optionally substituted by OH, or
 halo-$C_{1-6}$-alkoxy;
$R^5$ and $R^{5'}$ are each independently hydrogen or methyl;
$R^6$ is hydrogen or $C_{1-6}$-alkyl;
$R^7$, $R^{7'}$, $R^8$, $R^{8'}$, and $R^9$ are each independently selected from
 hydrogen,
 halo,
 halo-$C_{1-6}$-alkyl,
 $C_{1-6}$-alkyl,
 $C_{1-6}$-alkoxy,
 halo-$C_{1-6}$-alkoxy,
 nitro, and
 cyano,
 or $R^7$ and $R^8$, $R^{7'}$ and $R^{8'}$, $R^8$ and $R^9$, or $R^{8'}$ and $R^9$ are bound
  together to form a ring with the phenyl moiety, wherein
  —$R^7$—$R^8$— or —$R^{7'}$—$R^{8'}$— is
   —N($R^{10}$)—N=CH— or —CH=N—N($R^{10}$)—,
    wherein $R^{10}$ is hydrogen or $C_{1-6}$-alkyl,
   —N($R^{11}$)—CH=CH— or —CH=CH—N($R^{11}$)—,
    wherein $R^{11}$ is hydrogen or $C_{1-6}$-alkyl,
   —C($R^{12}$)=C($R^{13}$)—C($R^{14}$)=C($R^{15}$)—,
    wherein $R^{12}$, $R^{13}$, $R^{14}$, and $R^{15}$ are each independently selected from hydrogen, halo, halo-$C_{1-6}$-alkyl, $C_{1-6}$-alkyl, $C_{1-6}$-alkoxy, halo-$C_{1-6}$-alkoxy, nitro, and cyano,
   —O—(C$R^{16}$$R^{16'}$)$_n$—O—,
    wherein n is 1 or 2, and $R^{16}$ and $R^{16'}$ are each independently hydrogen, halo or $C_{1-6}$-alkyl,
   —N($R^{17}$)—CH=N— or —N=CH—N($R^{17}$)—
    wherein $R^{17}$ is hydrogen or $C_{1-6}$-alkyl, or
   —N($R^{18}$)—C(O)—$CH_2$— or —$CH_2$—C(O)—N($R^{18}$)—,
    wherein $R^{18}$ is hydrogen or $C_{1-6}$-alkyl,
or a pharmaceutically acceptable salt thereof.

The compounds of formula (I) can be manufactured by the methods given below, by the methods given in the examples or by analogous methods. Appropriate reaction conditions for the individual reaction steps are known to a person skilled in the art. Starting materials are either commercially available or can be prepared by methods analogous to the methods given below, by methods described in references cited in the text or in the examples, or by methods known in the art.

The compounds of formula (I) possess pharmaceutical activity, in particular they are modulators of V1a receptor activity. More particular, the compounds are antagonists of the V1a receptor. Such antagonists are useful as therapeutics in the conditions of dysmenorrhea, hypertension, chronic heart failure, inappropriate secretion of vasopressin, liver cirrhosis, nephrotic syndrome, obsessive compulsive disorder, anxiety and depressive disorders. The preferred indications with regard to the present invention are the treatment of anxiety and depressive disorders.

DETAILED DESCRIPTION OF THE INVENTION

The following definitions of the general terms used in the present description apply irrespective of whether the terms in question appear alone or in combination. It must be noted that, as used in the specification and the appended claims, the singular forms "a", "an," and "the" include plural forms unless the context clearly dictates otherwise.

In the present description, the term "alkyl", alone or in combination with other groups, refers to a branched or straight-chain monovalent saturated hydrocarbon radical. The term "$C_{1-6}$-alkyl" denotes a saturated straight- or branched-chain hydrocarbon group containing from 1 to 6 carbon atoms, for example, methyl, ethyl, n-propyl, isopropyl, n-butyl, isobutyl, tert-butyl, the isomeric pentyls and the like. A preferred sub-group of $C_{1-6}$-alkyl is $C_{1-4}$-alkyl, i.e. with 1-4 carbon atoms.

In the present invention, the term "alkylene" refers to a linear or branched saturated divalent hydrocarbon radical. In particular, "$C_{1-6}$-alkylene" means a linear saturated divalent hydrocarbon radical of one to six carbon atoms or a branched saturated divalent hydrocarbon radical of three to six carbon atoms, e.g. methylene, ethylene, 2,2-dimethylethylene, n-propylene, 2-methylpropylene, and the like.

In the present description, the term "alkoxy" and "$C_{1-6}$-alkoxy" refers to the group R'—O—, wherein R' is alkyl or $C_{1-6}$-alkyl as defined above. Examples of alkoxy groups are methoxy, ethoxy, n-propoxy, isopropoxy, n-butoxy, tert-butoxy, sec-butoxy and the like. A preferred sub-group of $C_{1-6}$-alkoxy, and still more preferred alkoxy groups are methoxy and/or ethoxy.

In the present description, the term "thioalkyl" and "$C_{1-6}$-thioalkyl" refers to the group R'—S—, wherein R' is alkyl or $C_{1-6}$-alkyl as defined above.

The term "$C_{1-6}$-hydroxyalkyl" or "$C_{1-6}$-alkyl substituted by OH" denotes a $C_{1-6}$-alkyl group as defined above wherein at least one of the hydrogen atoms of the alkyl group is replaced by a hydroxyl group.

The term "$C_{1-6}$-cyanoalkyl" or "$C_{1-6}$-alkyl substituted by CN" denotes a $C_{1-6}$-alkyl group as defined above wherein at least one of the hydrogen atoms of the alkyl group is replaced by a CN group.

The term "halo" or "halogen" refers to fluorine (F), chlorine (Cl), bromine (Br) and iodine (I) with fluorine, chlorine and bromine being preferred.

The term "halo-$C_{1-6}$-alkyl" is synonymous with "$C_{1-6}$-haloalkyl" or "$C_{1-6}$-alkyl substituted by halo" and means a $C_{1-6}$-alkyl group as defined above wherein at least one of the hydrogen atoms of the alkyl group is replaced by a halogen atom, preferably fluoro or chloro, most preferably fluoro. Examples of halo-$C_{1-6}$-alkyl include but are not limited to methyl, ethyl, propyl, isopropyl, isobutyl, sec-butyl, tert-butyl, pentyl or n-hexyl substituted by one or more Cl, F, Br or I atom(s) as well as those groups specifically illustrated by the examples herein below. Among the preferred halo-$C_{1-6}$-alkyl groups are difluoro- or trifluoro-methyl or -ethyl.

The term "halo-$C_{1-6}$-alkoxy" is synonymous with "$C_{1-6}$-haloalkoxy" or "$C_{1-6}$-alkoxy substituted by halo" and means a $C_{1-6}$-alkoxy group as defined above wherein at least one of the hydrogen atoms of the alkyl group is replaced by a halogen atom, preferably fluoro or chloro, most preferably fluoro. Among the preferred halogenated alkoxy groups are difluoro- or trifluoro-methoxy or -ethoxy.

The term "$C_{2-12}$-alkenyl", alone or in combination, denotes a straight-chain or branched hydrocarbon residue of 2 to 12 carbon atoms comprising at least one double bond. A preferred sub-group of $C_{2-12}$-alkenyl is $C_{2-6}$-alkenyl. Examples of the preferred alkenyl groups are ethenyl, propen-1-yl, propen-2-yl(allyl), buten-1-yl, buten-2-yl, buten-3-yl, penten-1-yl, penten-2-yl, penten-3-yl, penten-4-yl, hexen-1-yl, hexen-2-yl, hexen-3-yl, hexen-4-yl and hexen-5-yl, as well as those specifically illustrated by the examples herein below.

The term "one or more" substituents preferably means one, two or three optional substituents per ring.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

"Therapeutically effective amount" means an amount that is effective to prevent, alleviate or ameliorate symptoms of disease or prolong the survival of the subject being treated.

The term "bound together to form a ring with the phenyl moiety" means that the residues of the phenyl ring, which are located in ortho-position to each other, may form an anellated ring to the phenyl moiety.

The invention further comprises individual optical isomers of the compounds herein as well as racemic and non-racemic mixtures thereof.

In detail, the present invention relates to compounds of formula (I)

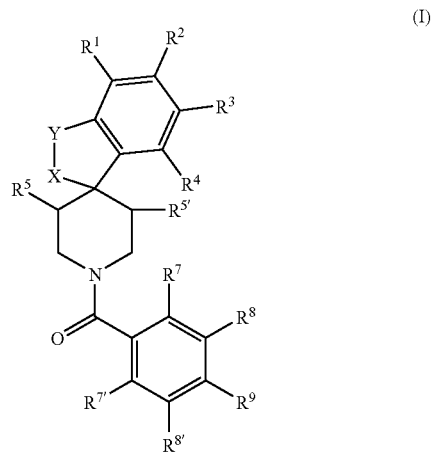

(I)

wherein
X is O and Y is C═O,
X is O and Y is $CH_2$,

X is C=O and Y is $NR^6$,
X is $CH_2$ and Y is O,
X—Y is CH=CH,
X—Y is $CH_2$—$CH_2$,
X is C=O and Y is O, or
X is $CH_2$ and Y is $NR^6$;
$R^1$, $R^2$, $R^3$ and $R^4$ are each independently
  hydrogen,
  halo,
  $C_{1-6}$-alkyl, optionally substituted by OH,
  halo-$C_{1-6}$-alkyl,
  $C_{1-6}$-alkoxy, optionally substituted by OH, or
  halo-$C_{1-6}$-alkoxy;
$R^5$ and $R^{5'}$ are each independently hydrogen or methyl;
$R^6$ is hydrogen or $C_{1-6}$-alkyl;
$R^7$, $R^{7'}$, $R^8$, $R^{8'}$, and $R^9$ are each independently selected from
  hydrogen,
  halo,
  halo-$C_{1-6}$-alkyl,
  $C_{1-6}$-alkyl,
  $C_{1-6}$-alkoxy,
  halo-$C_{1-6}$-alkoxy,
  nitro, and
  cyano,
  or $R^7$ and $R^8$, $R^{7'}$ and $R^{8'}$, $R^8$ and $R^9$, or $R^{8'}$ and $R^9$ are bound
    together to form a ring with the phenyl moiety, wherein
    —$R^7$—$R^8$— or —$R^{7'}$—$R^{8'}$— is
    —$N(R^{10})$—N=CH— or —CH=N—$N(R^{10})$—,
      wherein $R^{10}$ is hydrogen or $C_{1-6}$-alkyl,
    —$N(R^{11})$—CH=CH— or —CH=CH—$N(R^{12})$—,
      wherein $R^{11}$ is hydrogen or $C_{1-6}$-alkyl,
    —$C(R^{12})$=$C(R^{13})$—$C(R^{14})$=$C(R^{15})$—,
      wherein $R^{12}$, $R^{13}$, $R^{14}$, and $R^{15}$ are each independently selected from hydrogen, halo, halo-$C_{1-6}$-alkyl, $C_{1-6}$-alkyl, $C_{1-6}$-alkoxy, halo-$C_{1-6}$-alkoxy, nitro, and cyano,
    —O—$(CR^{16}R^{16'})_n$—O—,
      wherein n is 1 or 2, and $R^{16}$ and $R^{16'}$ are each independently hydrogen, halo or $C_{1-6}$-alkyl,
    —$N(R^{17})$—CH=N— or —N=CH—$N(R^{17})$—
      wherein $R^{17}$ is hydrogen or $C_{1-6}$-alkyl, or
    —$N(R^{18})$—C(O)—$CH_2$— or —$CH_2$—C(O)—$N(R^{18})$—,
      wherein $R^{18}$ is hydrogen or $C_{1-6}$-alkyl,
or a pharmaceutically acceptable salt thereof.

In certain embodiments of the invention, $R^1$, $R^2$, $R^3$ and $R^4$ are each independently hydrogen, halo, $C_{1-6}$-alkyl or $C_{1-6}$-alkoxy, optionally substituted by OH.

In certain embodiments of the invention, $R^1$ is hydrogen or halo, preferably hydrogen or fluoro.

In certain embodiments of the invention, $R^2$ is hydrogen, halo or $C_{1-6}$-alkoxy; preferably hydrogen, fluoro, bromo or methoxy.

In certain embodiments of the invention, $R^3$ is hydrogen, halo, or $C_{1-6}$-alkoxy, optionally substituted by OH; preferably hydrogen, chloro, bromo, methoxy or —$O(CH_2)_2OH$.

In certain embodiments of the invention, $R^4$ is hydrogen or $C_{1-6}$-alkyl; preferably hydrogen or methyl.

In certain embodiments all $R^1$ to $R^4$ are hydrogen.

In certain embodiments, one residue of $R^1$ to $R^4$ is halo and the others are hydrogen.

In certain embodiments, one residue of $R^1$ to $R^4$ is $C_{1-6}$-alkyl, preferably methyl, and the others are hydrogen.

In certain embodiments, one residue of $R^1$ to $R^4$ is $C_{1-6}$-alkoxy, optionally substituted by OH, preferably methoxy or —$O(CH_2)_2OH$, and the others are hydrogen.

In certain embodiments of the invention, $R^5$ and $R^{5'}$ are both hydrogen, in other embodiments of the invention, $R^5$ and $R^{5'}$ are both methyl, in other embodiments of the invention, $R^5$ is hydrogen and $R^{5'}$ is methyl.

In certain embodiments of the invention, $R^5$ is hydrogen, $R^{5'}$ is methyl, X is O and Y is C=O.

In certain embodiments of the invention, $R^6$ is hydrogen or $C_{1-6}$-alkyl, preferably hydrogen.

In certain embodiments of the invention, both $R^7$ and $R^{7'}$ are hydrogen.

In certain embodiments of the invention, one of $R^7$ and $R^{7'}$ is hydrogen and the other is halo, halo-$C_{1-6}$-alkyl, $C_{1-6}$-alkyl, $C_{1-6}$-alkoxy, halo-$C_{1-6}$-alkoxy, nitro, or cyano.

In certain embodiments of the invention, $R^7$ and $R^{7'}$ are each independently hydrogen or halo.

In certain embodiments of the invention, one of $R^7$ and $R^{7'}$ is hydrogen and the other is halo, preferably chloro.

In certain embodiments of the invention, each of $R^8$ and $R^{8'}$ are independently hydrogen, halo, halo-$C_{1-6}$-alkyl, $C_{1-6}$-alkyl, $C_{1-6}$-alkoxy, halo-$C_{1-6}$-alkoxy, nitro, or cyano.

In certain embodiments of the invention, $R^8$ and $R^{8'}$ are each independently hydrogen, halo, or $C_{1-6}$-alkoxy, preferably hydrogen, chloro, ethoxy or methoxy.

In certain embodiments of the invention, $R^7$ and $R^8$ or $R^{7'}$ and $R^{8'}$ are bound together to form a ring with the phenyl moiety, wherein
    —$R^7$—$R^8$— or —$R^{7'}$—$R^{8'}$— is
    —$N(R^{10})$—N=CH— or —CH=N—$N(R^{10})$—,
      wherein $R^{10}$ is hydrogen or $C_{1-6}$-alkyl,
    —$N(R^{11})$—CH=CH— or —CH=CH—$N(R^{12})$—,
      wherein $R^{11}$ is hydrogen or $C_{1-6}$-alkyl,
    —$C(R^{12})$=$C(R^{13})$—$C(R^{14})$=$C(R^{15})$—,
      wherein $R^{12}$, $R^{13}$, $R^{14}$, and $R^{15}$ are each independently selected from hydrogen, halo, halo-$C_{1-6}$-alkyl, $C_{1-6}$-alkyl, $C_{1-6}$-alkoxy, halo-$C_{1-6}$-alkoxy, nitro, and cyano,
    —O—$(CR^{16}R^{16'})_n$—O—,
      wherein n is 1 or 2, and $R^{16}$ and $R^{16'}$ are each independently hydrogen, halo or $C_{1-6}$-alkyl, or
    —$N(R^{17})$—CH=N— or —N=CH—$N(R^{17})$—,
      wherein $R^{17}$ is hydrogen or $C_{1-6}$-alkyl.

In certain embodiments of the invention, $R^7$ and $R^8$ are bound together to form a ring with the phenyl moiety as described above, and
    $R^9$, $R^{8'}$ and $R^{7'}$ are hydrogen,
    $R^9$ and $R^{7'}$ are hydrogen, and $R^{8'}$ is halo, preferably chloro, or
    $R^9$ and $R^{7'}$ are hydrogen, and $R^{8'}$ is $C_{1-6}$-alkoxy, preferably ethoxy or methoxy.

In certain embodiments of the invention, $R^{7'}$ and $R^{8'}$ are bound together to form a ring with the phenyl moiety as described above, and
    $R^9$, $R^8$ and $R^7$ are hydrogen,
    $R^9$ and $R^7$ are hydrogen, and $R^8$ is halo, preferably chloro, or
    $R^9$ and $R^7$ are hydrogen, and $R^8$ is $C_{1-6}$-alkoxy, preferably ethoxy or methoxy.

In certain embodiments of the invention, $R^7$ and $R^8$ are halo, preferably chloro, and $R^9$, $R^{7'}$ and $R^{8'}$ are hydrogen.

In certain embodiments of the invention, $R^9$ is hydrogen, halo, halo-$C_{1-6}$-alkyl, $C_{1-6}$-alkyl, $C_{1-6}$-alkoxy, halo-$C_{1-6}$-alkoxy, nitro, or cyano.

In certain embodiments of the invention, $R^9$ is hydrogen, halo, or $C_{1-6}$-alkyl, preferably hydrogen, chloro or tert-butyl.

In certain embodiments of the invention,
$R^8$ and $R^9$ or $R^{8'}$ and $R^9$ are bound together to form a ring with the phenyl moiety, wherein
—$R^8$—$R^9$— or —$R^{8'}$—$R^9$— is
—C($R^{12}$)=C($R^{13}$)—C($R^{14}$)=C($R^{15}$)
wherein $R^{12}$, $R^{13}$, $R^{14}$, and $R^{15}$ are each independently selected from hydrogen, halo, halo-$C_{1-6}$-alkyl, $C_{1-6}$-alkyl, $C_{1-6}$-alkoxy, halo-$C_{1-6}$-alkoxy, nitro, and cyano,
—N($R^{18}$)—C(O)—CH$_2$— or —CH$_2$—C(O)—N($R^{18}$)—,
wherein $R^{18}$ is hydrogen or $C_{1-6}$-alkyl.

In certain embodiments of the invention, $R^8$ and $R^9$ are bound together to form a ring with the phenyl moiety as described above, and $R^7$, $R^{8'}$ and $R^{7'}$ are hydrogen.

In certain embodiments of the invention, $R^{8'}$ and $R^9$ are bound together to form a ring with the phenyl moiety as described above, and $R^7$, $R^8$ and $R^{7'}$ are hydrogen.

In certain embodiments of the invention, $R^8$ and $R^9$ are halo, preferably chloro, and $R^7$, $R^{7'}$ and $R^{8'}$ are hydrogen.

In certain embodiments of the invention, $R^{8'}$ and $R^9$ are halo, preferably chloro, and $R^7$, $R^{7'}$ and $R^{8''}$ are hydrogen.

In certain embodiments of the invention, $R^9$ is $C_{1-6}$-alkyl or halo, preferably tert-butyl or chloro, and $R^7$, $R^{7'}$, $R^8$, and $R^{8'}$ are hydrogen.

Preferred compounds of the invention are those of formula (I) wherein
$R^8$ and $R^9$ are halo, or wherein
$R^8$ and $R^9$ are bound together to form a ring with the phenyl moiety, wherein
—$R^8$—$R^9$— is
—C($R^{12}$)=C($R^{13}$)—C($R^{14}$)=C($R^{15}$)
wherein $R^{12}$, $R^{13}$, $R^{14}$, and $R^{15}$ are each independently selected from hydrogen, halo, halo-$C_{1-6}$-alkyl, $C_{1-6}$-alkyl, $C_{1-6}$-alkoxy, halo-$C_{1-6}$-alkoxy, nitro, and cyano,
and $R^7$, $R^{7'}$ and $R^{8'}$ are hydrogen.

Preferred compounds of the invention are those of formula (I) wherein
$R^{8'}$ and $R^9$ are halo, or wherein
$R^{8'}$ and $R^9$ are bound together to form a ring with the phenyl moiety, wherein
—$R^{8'}$—$R^9$— is
—C($R^{12}$)=C($R^{13}$)—C($R^{14}$)=C($R^{15}$)—,
wherein $R^{12}$, $R^{13}$, $R^{14}$, and $R^{15}$ are each independently selected from hydrogen, halo, halo-$C_{1-6}$-alkyl, $C_{1-6}$-alkyl, $C_{1-6}$-alkoxy, halo-$C_{1-6}$-alkoxy, nitro, and cyano,
and $R^7$, $R^{7'}$ and $R^8$ are hydrogen.

Preferably, $R^7$, $R^{7'}$, $R^8$, $R^{8'}$ and $R^9$ are not simultaneously hydrogen.

A certain embodiment of the invention relates to a compound of formula (I)

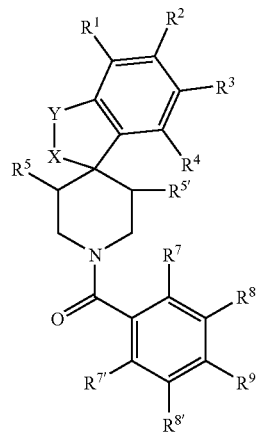

wherein
X is O and Y is C=O,
X is O and Y is CH$_2$,
X is C=O and Y is NR$^6$,
X is CH$_2$ and Y is O; or
X—Y is CH=CH, or
X—Y is CH$_2$—CH$_2$, or
X is C=O and Y is O, or
X is CH$_2$ and Y is NR$^6$;
$R^1$, $R^2$, $R^3$ and $R^4$ are each independently
hydrogen,
halo,
$C_{1-6}$-alkyl, optionally substituted by OH,
halo-$C_{1-6}$-alkyl,
$C_{1-6}$-alkoxy, optionally substituted by OH, or
halo-$C_{1-6}$-alkoxy;
$R^5$ and $R^{5'}$ are each independently hydrogen or methyl;
$R^6$ is hydrogen or $C_{1-6}$-alkyl;
$R^7$ and $R^{7'}$ are each independently selected from
hydrogen,
halo,
halo-$C_{1-6}$-alkyl,
$C_{1-6}$-alkyl,
$C_{1-6}$-alkoxy,
halo-$C_{1-6}$-alkoxy,
nitro, and
cyano;
$R^8$ and $R^{8'}$ are each independently selected from
hydrogen,
halo,
$C_{1-6}$-alkoxy,
halo-$C_{1-6}$-alkyl,
$C_{1-6}$-alkyl,
halo-$C_{1-6}$-alkoxy,
nitro, and
cyano;
$R^7$ and $R^8$ or $R^{7'}$ and $R^{8'}$ are bound together to form a ring with the phenyl moiety, wherein
—$R^7$—$R^8$— or —$R^{7'}$—$R^{8'}$— is
—N($R^{10}$)—N=CH—, or —CH=N—N($R^{10}$)—,
wherein $R^{10}$ is hydrogen or $C_{1-6}$-alkyl,
—N($R^{11}$)—CH=CH—, or —CH=CH—N($R^{11}$)—,
wherein $R^{11}$ is hydrogen or $C_{1-6}$-alkyl,
—C($R^{12}$)=C($R^{13}$)—C($R^{14}$)=C($R^{15}$)—,
wherein $R^{12}$, $R^{13}$, $R^{14}$, and $R^{15}$ are each independently selected from hydrogen, halo, halo-$C_{1-6}$-alkyl, $C_{1-6}$-alkyl, $C_{1-6}$-alkoxy, halo-$C_{1-6}$-alkoxy, nitro, and cyano, —O—(CR$^{16}$R$^{16'}$)$_n$—O—,
  wherein n is 1 or 2, and R$^{16}$ and R$^{16'}$ are each independently hydrogen, halo or C$_{1-6}$-alkyl,
—N(R$^{17}$)—CH=N—, or —N=CH—N(R$^{17}$)—,
  wherein R$^{17}$ is hydrogen or C$_{1-6}$-alkyl,
R$^9$ is hydrogen,
  halo,
  C$_{1-6}$-alkyl,
  halo-C$_{1-6}$-alkyl,
  C$_{1-6}$-alkoxy,
  halo-C$_{1-6}$-alkoxy,
  nitro, or
  cyano;
R$^8$ and R$^9$ or R$^{8'}$ and R$^9$ are bound together to form a ring with the phenyl moiety, wherein
  —R$^8$—R$^9$— or —R$^{8'}$—R$^9$— is
  —C(R$^{12}$)=C(R$^{13}$)—C(R$^{14}$)=C(R$^{15}$)
    wherein R$^{12}$, R$^{13}$, R$^{14}$, and R$^{15}$ are each independently selected from hydrogen, halo, halo-C$_{1-6}$-alkyl, C$_{1-6}$-alkyl, C$_{1-6}$-alkoxy, halo-C$_{1-6}$-alkoxy, nitro, and cyano,
  —N(R$^{18}$)—C(O)—CH$_2$—, or —CH$_2$—C(O)—N(R$^{18}$)—,
    wherein R$^{18}$ is hydrogen or C$_{1-6}$-alkyl,
or a pharmaceutically acceptable salt thereof.

A certain embodiment of the invention relates to compounds of formula (I)

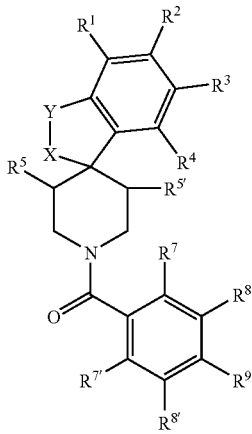

(I)

wherein
  X is O and Y is C=O,
  X is O and Y is CH$_2$,
  X is C=O and Y is NR$^6$,
  X is CH$_2$ and Y is O,
  X—Y is CH=CH,
  X—Y is CH$_2$—CH$_2$,
  X is C=O and Y is O, or
  X is CH$_2$ and Y is NR$^6$;
R$^1$, R$^2$, R$^3$ and R$^4$ are each independently
  hydrogen,
  halo, or
  C$_{1-6}$-alkoxy, optionally substituted by OH,
R$^5$ and R$^{5'}$ are each independently hydrogen or methyl;
R$^6$ is hydrogen or C$_{1-6}$-alkyl;
R$^7$ and R$^{7'}$ are each independently hydrogen or halo;
R$^8$ and R$^{8'}$ are each independently hydrogen, halo, or C$_{1-6}$-alkoxy;

R$^7$ and R$^8$ or R$^{7'}$ and R$^{8'}$ are bound together to form a ring with the phenyl moiety, wherein
  —R$^7$—R$^8$— or —R$^{7'}$—R$^{8'}$— is
  —N(R$^{10}$)—N=CH— or —CH=N—N(R$^{10}$)—,
    wherein R$^{10}$ is hydrogen or C$_{1-6}$-alkyl,
  —N(R$^{11}$)—CH=CH— or —CH=CH—N(R$^{11}$)—,
    wherein R$^{11}$ is hydrogen or C$_{1-6}$-alkyl,
  —C(R$^{12}$)=C(R$^{13}$)—C(R$^{14}$)=C(R$^{15}$)—,
    wherein R$^{12}$, R$^{13}$ R$^{14}$ and R$^{15}$ are each independently selected from hydrogen, halo, halo-C$_{1-6}$-alkyl, C$_{1-6}$-alkyl, C$_{1-6}$-alkoxy, halo-C$_{1-6}$-alkoxy, nitro, and cyano,
  —O—(CR$^{16}$R$^{16'}$)$_n$—O—,
    wherein n is 1 or 2, and R$^{16}$ and R$^{16'}$ are each independently hydrogen, halo or C$_{1-6}$-alkyl,
  —N(R$^{17}$)—CH=N— or —N=CH—N(R$^{17}$)—,
    wherein R$^{17}$ is hydrogen or C$_{1-6}$-alkyl,
R$^9$ is hydrogen, halo, or C$_{1-6}$-alkyl;
R$^8$ and R$^9$ or R$^{8'}$ and R$^9$ are bound together to form a ring with the phenyl moiety, wherein
  —R$^8$—R$^9$— or —R$^{8'}$—R$^9$— is
  —C(R$^{12}$)=C(R$^{13}$)—C(R$^{14}$)=C(R$^{15}$)
    wherein R$^{12}$, R$^{13}$, R$^{14}$, and R$^{15}$ are each independently selected from hydrogen, halo, halo-C$_{1-6}$-alkyl, C$_{1-6}$-alkyl, C$_{1-6}$-alkoxy, halo-C$_{1-6}$-alkoxy, nitro, and cyano,
  —N(R$^{18}$)—C(O)—CH$_2$— or —CH$_2$—C(O)—N(R$^{18}$)—,
    wherein R$^{18}$ is hydrogen or C$_{1-6}$-alkyl,
or a pharmaceutically acceptable salt thereof.

In one embodiment, the invention provides compounds of formula I wherein
  X is O and Y is C=O,
  X is O and Y is CH$_2$,
  X is CH$_2$ and Y is O, or
  X is C=O and Y is O.

In one embodiment, the invention provides compounds of formula I wherein
  X is C=O and Y is NR$^6$, or
  X is CH$_2$ and Y is NR$^6$.

In one embodiment, the invention provides compounds of formula I wherein
  X is C=O and Y is NR$^6$, or
  X is CH$_2$ and Y is NR$^6$.

An embodiment of the invention relates to compounds of formula (I-a)

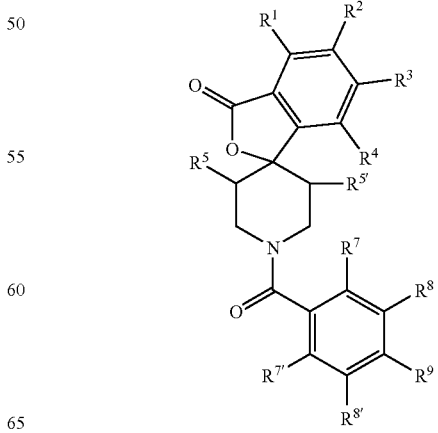

(I-a)

wherein $R^1$ to $R^{5'}$ and $R^7$ to $R^9$ are as defined in any combination as described above.

An embodiment of the invention relates to compounds of formula (I-b)

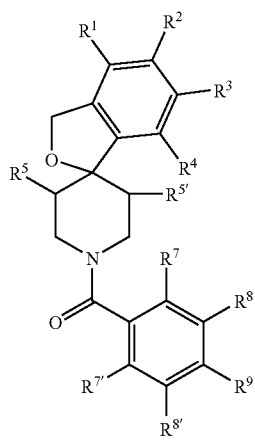

(I-b)

wherein $R^1$ to $R^{5'}$ and $R^7$ to $R^9$ are as defined in any combination as described above.

An embodiment of the invention relates to compounds of formula (I-c)

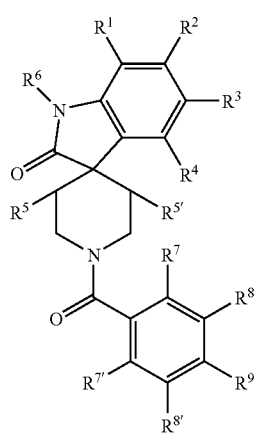

(I-c)

wherein $R^1$ to $R^9$ are as defined in any combination as described above.

An embodiment of the invention relates to compounds of formula (I-d)

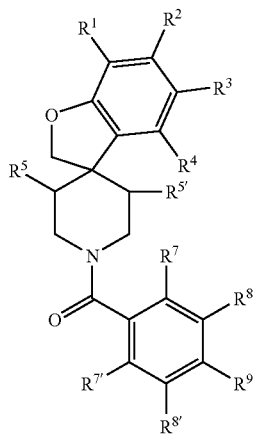

(I-d)

wherein $R^1$ to $R^{5'}$ and $R^7$ to $R^9$ are as defined in any combination as described above.

An embodiment of the invention relates to compounds of formula (I-e)

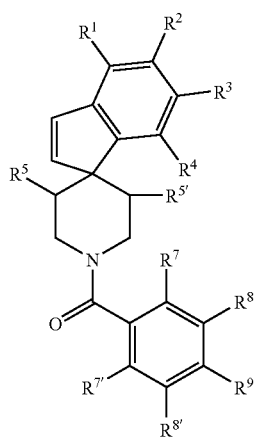

(I-e)

wherein $R^1$ to $R^{5'}$ and $R^7$ to $R^9$ are as defined in any combination as described above.

An embodiment of the invention relates to compounds of formula (I-f)

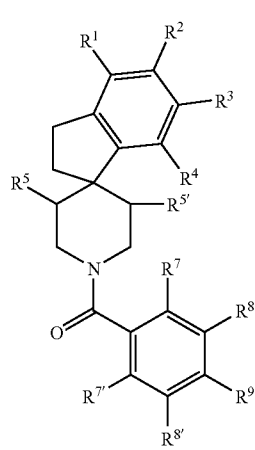

(I-f)

wherein $R^1$ to $R^{5'}$ and $R^7$ to $R^9$ are as defined in any combination as described above.

An embodiment of the invention relates to compounds of formula (I-g)

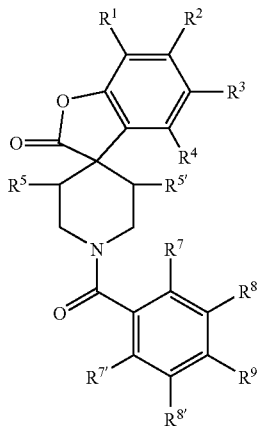

(I-g)

wherein $R^1$ to $R^{5'}$ and $R^7$ to $R^9$ are as defined in any combination as described above.

An embodiment of the invention relates to compounds of formula (I-h)

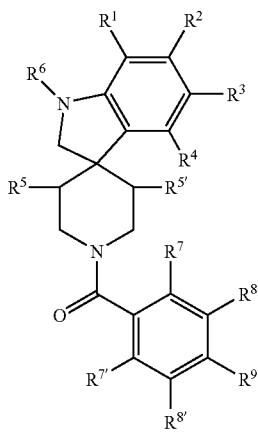

(I-h)

wherein $R^1$ to $R^9$ are as defined in any combination as described above.

Any compound of formula (I-a) to (I-h) may be combined with any residue or combination of residues $R^1$ to $R^9$ as defined above.

Preferred compounds are those of formula (I-a) to (I-f).

Preferred compounds of the invention are those of the examples. More preferred are the following compounds:

6-Methoxy-1'-(2-naphthoyl)-3H-spiro[2-benzofuran-1,4'-piperidin]-3-one,

1'-(3,4-Dichlorobenzoyl)-3H-spiro[2-benzofuran-1,4'-piperidin]-3-one,

1'-(3,4-Dichlorobenzoyl)-6-methoxy-3H-spiro[2-benzofuran-1,4'-piperidin]-3-one,

1'-(3,4-Dichlorobenzoyl)-5-methoxy-3H-spiro[2-benzofuran-1,4'-piperidin]-3-one,

1'-(3,4-Dichlorobenzoyl)-5-fluoro-3H-spiro[2-benzofuran-1,4'-piperidin]-3-one,

1'-(3,4-Dichlorobenzoyl)-6-(2-hydroxyethoxy)-3H-spiro[2-benzofuran-1,4'-piperidin]-3-one, 1'-(4-tert-Butylbenzoyl)-3H-spiro[2-benzofuran-1,4'-piperidine], 1'-[(5-Methoxy-1H-indol-7-yl)carbonyl]-3H-spiro[2-benzofuran-1,4'-piperidine], 5-Bromo-1'-(2-naphthoyl)spiro[indole-3,4'-piperidin]-2(1H)-one, 1'-(2-Naphthoyl)spiro[indene-1,4'-piperidine]-1, and 1'-(3,4-Dichlorobenzoyl)-2,3-dihydrospiro[indene-1,4'-piperidine].

The invention also encompasses methods for the treatment of dysmenorrhea, hypertension, chronic heart failure, inappropriate secretion of vasopressin, liver cirrhosis, nephrotic syndrome, obsessive compulsive disorder, anxiety and depressive disorders which comprises administering an effective amount of a compound of formula (I), (I-a), (I-b), (I-c), (I-d), (I-e), (I-f), (I-g) or (I-h).

The invention also encompasses a pharmaceutical composition comprising a compound of formula (I), (I-a), (I-b), (I-c), (I-d), (I-e), (I-f), (I-g) or (I-h) and a pharmaceutically acceptable carrier. The pharmaceutical composition may further comprise at least one pharmaceutically acceptable excipient.

In a certain embodiment, the compound of the invention can be manufactured according to a process comprising reacting a compound of formula (II):

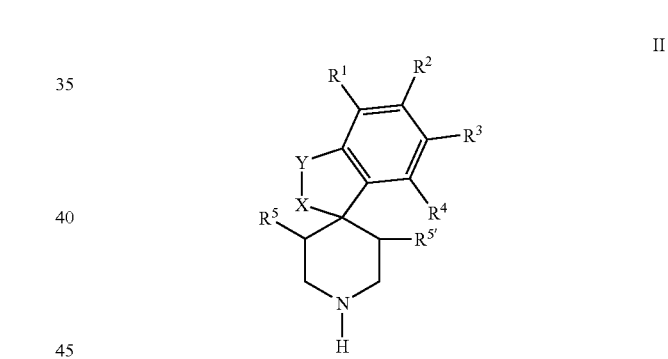

II with an acid chloride of formula (III-b)

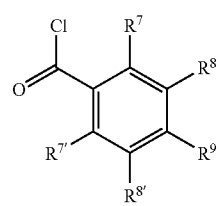

III-b to obtain the compound according to formula (I) wherein $R^1$ to $R^{10}$ and X and Y are as defined above.

In a certain embodiment, the compound of the invention can be manufactured according to a process comprising reacting a compound of formula (II):

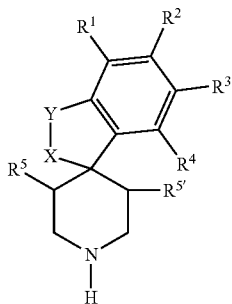

with an acid of formula (III-a)

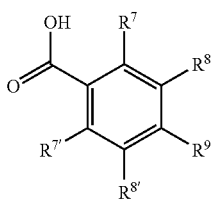

to obtain the compound of formula (I) wherein $R^1$ to $R^{10}$ and X and Y are as defined above.

The synthesis of compounds of general formula (I) will be described in more detail below and in the examples.

The compounds of the present invention exhibit V1a activity, which may be detected as described below:

V1a Activity

Material & Method:

The human V1a receptor was cloned by RT-PCR from total human liver RNA. The coding sequence was subcloned in an expression vector after sequencing to confirm the identity of the amplified sequence. To demonstrate the affinity of the compounds from the present invention to the human V1a receptor binding studies were performed. Cell membranes were prepared from HEK293 cells transiently transfected with the expression vector and grown in 20 liter fermenters with the following protocol.

50 g of cells were resuspended in 30 ml freshly prepared ice cold Lysis buffer (50 mM HEPES, 1 mM EDTA, 10 mM MgCl2 adjusted to pH=7.4+complete cocktail of protease inhibitor (Roche Diagnostics)); homogenized with Polytron for 1 min; and sonicated on ice for 2×2 minutes at 80% intensity (Vibracell sonicator). The preparation was centrifuged 20 min at 500 g at 4° C., the pellet was discarded and the supernatant centrifuged 1 hour at 43,000 g at 4° C. (19,000 rpm). The pellet was resuspended in 12.5 ml Lysis buffer+ 12.5 ml Sucrose 20% and homogenized using a Polytron for 1-2 min. The protein concentration was determined by the Bradford method, and aliquots were stored at −80° C. until use. For binding studies 60 mg Yttrium silicate SPA beads (Amersham) were mixed with an aliquot of membrane in binding buffer (50 mM Tris, 120 mM NaCl, 5 mM KCl, 2 mM CaCl2, 10 mM MgCl2) for 15 minutes with mixing. 50 ul of bead/membrane mixture was then added to each well of a 96 well plate, followed by 50 ul of 4 nM 3H-Vasopressin (American Radiolabeled Chemicals). For total binding measurement 100 ul of binding buffer were added to the respective wells, for non-specific binding 100 ul of 8.4 mM cold vasopressin and for compound testing 100 ul of a serial dilution of each compound in 2% DMSO. The plate was incubated 1 h at room temperature, centrifuged 1 min at 1000 g and counted on a Packard Top-Count. Non-specific binding counts were subtracted from each well and data was normalized to the maximum specific binding set at 100%. To calculate an IC 50 the curve was fitted using a non-linear regression model (XLfit), and the Ki was calculated using the Cheng-Prussoff equation.

| Ex | pKi hV1a |
|----|----------|
| 1  | 8.08 |
| 6  | 7.72 |
| 7  | 7.54 |
| 9  | 7.32 |
| 11 | 7.53 |
| 12 | 7.66 |
| 25 | 7.2 |
| 27 | 7.3 |
| 33 | 6.96 |
| 36 | 7.05 |
| 42 | 6.95 |

The present invention also provides pharmaceutical compositions containing compounds of the invention, such as compounds of formula (I), and (Ia) to (If), or pharmaceutically acceptable salts thereof and a pharmaceutically acceptable carrier. Such pharmaceutical compositions can be in the form of tablets, coated tablets, dragées, hard and soft gelatine capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers.

Lactose, corn starch or derivatives thereof, talc, stearic acid or its salts etc can be used as such excipients e.g. for tablets, dragées and hard gelatine capsules. Suitable excipients for soft gelatine capsules are e.g. vegetable oils, waxes, fats, semi-solid and liquid polyols etc. Suitable excipients for the manufacture of solutions and syrups are e.g. water, polyols, saccharose, invert sugar, glucose etc. Suitable excipients for injection solutions are e.g. water, alcohols, polyols, glycerol, vegetable oils etc. Suitable excipients for suppositories are e.g. natural or hardened oils, waxes, fats, semi-liquid or liquid polyols etc.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage at which a compound of the invention can be administered can vary within wide limits and will, of course, be fitted to the individual requirements in each particular case. In general, in the case of oral administration a daily dosage of about 10 to 1000 mg per person of a compound of general formula (I) should be appropriate, although the above upper limit can also be exceeded when necessary.

The following Examples illustrate the present invention without limiting it. All temperatures are given in degrees Celsius.

EXAMPLE A

Tablets of the following composition can be manufactured in the usual manner:

|  | mg/tablet |
| --- | --- |
| Active substance | 5 |
| Lactose | 45 |
| Corn starch | 15 |
| Microcrystalline cellulose | 34 |
| Magnesium stearate | 1 |
| Tablet weight | 100 |

EXAMPLE B

Capsules of the following composition are manufactured:

|  | mg/capsule |
| --- | --- |
| Active substance | 10 |
| Lactose | 155 |
| Corn starch | 30 |
| Talc | 5 |
| Capsule fill weight | 200 |

The active substance, lactose and corn starch can be firstly mixed in a mixer and then in a comminuting machine. The mixture the can be returned to the mixer, the talc can be added thereto and mixed thoroughly. The mixture can be filled by machine into hard gelatine capsules.

EXAMPLE C

Suppositories of the following composition can be manufactured:

|  | mg/supp. |
| --- | --- |
| Active substance | 15 |
| Suppository mass | 1285 |
| Total | 1300 |

The suppository mass can be melted in a glass or steel vessel, mixed thoroughly and cooled to 45° C.

Thereupon, the finely powdered active substance can be added thereto and stirred until it has dispersed completely. The mixture the can be poured into suppository moulds of suitable size, left to cool; the suppositories then can be removed from the moulds and packed individually in wax paper or metal foil.

In the following, the synthesis of compounds of formula (I) is further exemplified: The following general scheme A is an example of the preparation of the compounds of the invention according to general procedure 1:

General Scheme A

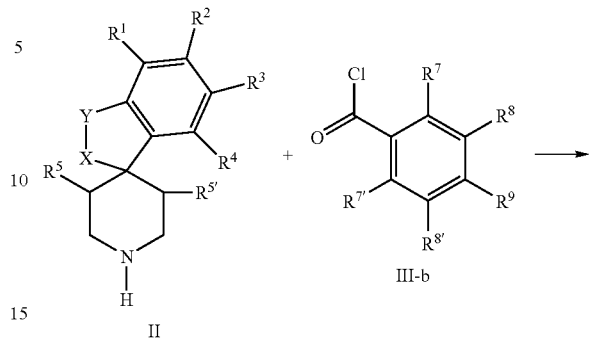

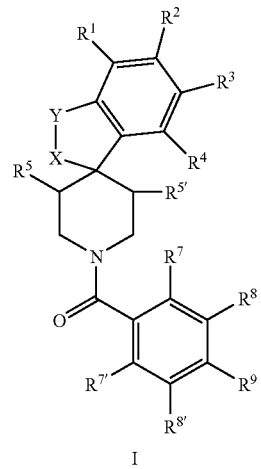

General Procedure 1—Amide Coupling with Acid Chlorides:

A solution of the amine (1 eq), the acid chloride (1 eq) and DIPEA (1.5 eq) in DMF is stirred at RT for 14 h. The mixture is concentrated and purified by preparative HPLC to yield the desired product.

The following general scheme B is an example of the preparation of the compounds of the invention according to general procedure 2:

General scheme B:

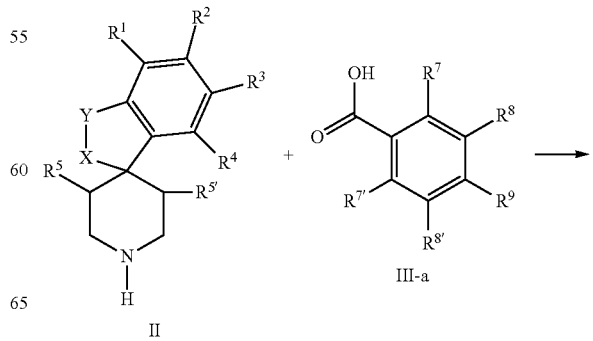

19
-continued

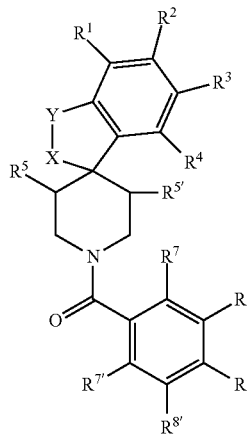

I

General Procedure 2—Amide Coupling with Carboxylic Acids:

A solution of the acid (1 eq) and HATU (1 eq) in DMF is shaken for 30 min at RT and then a solution of the amine (1 eq) and DIPEA (2 eq) in DMF is added and the mixture shaken at RT for 2 h. The mixture is concentrated and purified by preparative HPLC to yield the desired product.

EXAMPLES

Example 1

6-Methoxy-1'-(2-naphthoyl)-3H-spiro[2-benzofuran-1,4'-piperidin]-3-one

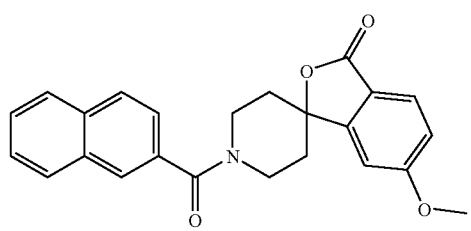

Amide coupling according to general procedure I:
  Amine: 6-methoxy-3H-spiro[2-benzofuran-1,4'-piperidin]-3-one (described in EP 722941)
  Acid chloride: Naphthalene-2-carbonyl chloride
  ES-MS m/e (%): 388.4 (M+H$^+$).

20

Example 2

1'-(4-tert-Butylbenzoyl)-6-chloro-3H-spiro[2-benzofuran-1,4'-piperidin]-3-one

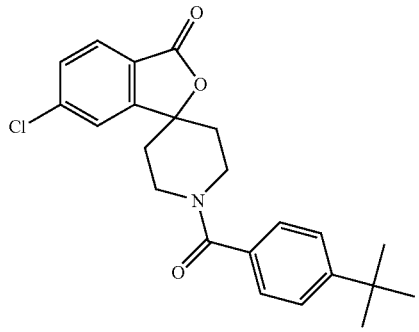

Amide coupling according to general procedure I:
  Amine: 6-chloro-3H-spiro[2-benzofuran-1,4'-piperidin]-3-one (described in EP 722941)
  Acid chloride: 4-tert-Butyl-benzoyl chloride
  ES-MS m/e (%): 398.4 (M+H$^+$).

Example 3

Rac-(1R,3'S)-1'-(4-tert-butylbenzoyl)-3'-methyl-3H-spiro[2-benzofuran-1,4'-piperidin]-3-one

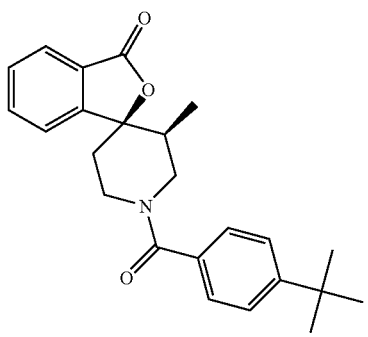

Amide coupling according to general procedure I:
  Amine: rac-(1R,3'S)-3'-methyl-3H-spiro[2-benzofuran-1,4'-piperidin]-3-one (described in WO 9929696)
  Acid chloride: 4-tert-Butyl-benzoyl chloride
  ES-MS m/e (%): 378.5 (M+H$^+$).

Example 4

1'-(4-tert-Butylbenzoyl)-3H-spiro[2-benzofuran-1,4'-piperidin]-3-one

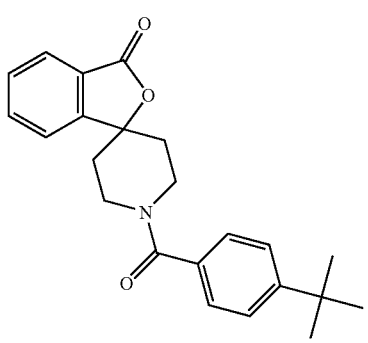

Amide coupling according to general procedure I:
Amine: 3H-spiro[2-benzofuran-1,4'-piperidin]-3-one (described in Journal of Organic Chemistry (1976), 41(15), 2628-33)
Acid chloride: 4-tert-Butyl-benzoyl chloride
ES-MS m/e (%): 364.5 (M+H$^+$).

Example 5

5-Methoxy-1'-(2-naphthoyl)-3H-spiro[2-benzofuran-1,4'-piperidin]-3-one

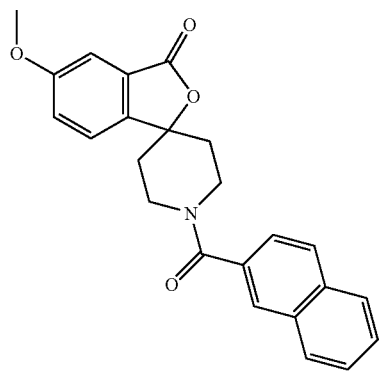

Amide coupling according to general procedure I:
Amine: 5-methoxy-3H-spiro[2-benzofuran-1,4'-piperidin]-3-one (described in EP 722941)
Acid chloride: Naphthalene-2-carbonyl chloride
ES-MS m/e (%): 388.5 (M+H$^+$).

Example 6

1'-(3,4-Dichlorobenzoyl)-3H-spiro[2-benzofuran-1,4'-piperidin]-3-one

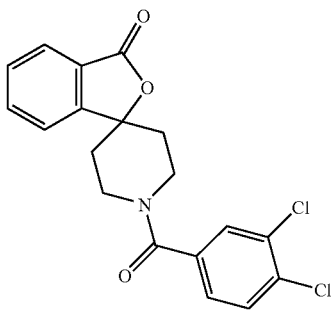

Amide coupling according to general procedure 2:
Amine: 3H-spiro[2-benzofuran-1,4'-piperidin]-3-one (described in Journal of Organic Chemistry (1976), 41(15), 2628-33)
Acid: 3,4-Dichloro-benzoic acid
ES-MS m/e (%): 376.4 (M+H$^+$).

Example 7

1'-(3,4-Dichlorobenzoyl)-6-methoxy-3H-spiro[2-benzofuran-1,4'-piperidin]-3-one

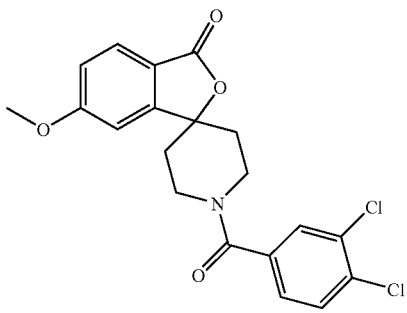

Amide coupling according to general procedure 2:
Amine: 6-methoxy-3H-spiro[2-benzofuran-1,4'-piperidin]-3-one (described in EP 722941)
Acid: 3,4-Dichloro-benzoic acid
ES-MS m/e (%): 406.4 (M+H$^+$).

Example 8

6-Chloro-1'-(3,4-dichlorobenzoyl)-3H-spiro[2-benzofuran-1,4'-piperidin]-3-one

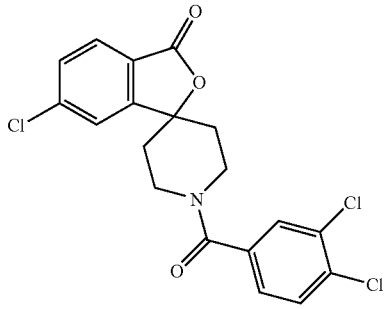

Amide coupling according to general procedure 2:
Amine: 6-chloro-3H-spiro[2-benzofuran-1,4'-piperidin]-3-one (described in EP 722941)
Acid: 3,4-Dichloro-benzoic acid
ES-MS m/e (%): 410.3 (M+H$^+$).

Example 9

1'-(3,4-Dichlorobenzoyl)-5-methoxy-3H-spiro[2-benzofuran-1,4'-piperidin]-3-one

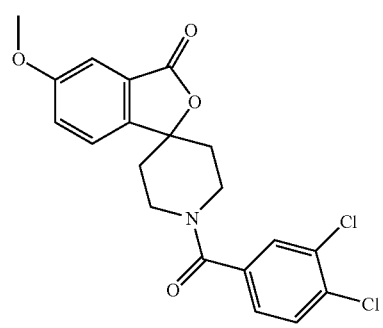

Amide coupling according to general procedure 2:
Amine: 5-methoxy-3H-spiro[2-benzofuran-1,4'-piperidin]-3-one (described in EP 722941)
Acid: 3,4-Dichloro-benzoic acid
ES-MS m/e (%): 406.4 (M+H$^+$).

Example 10

5-Bromo-1'-(3,4-dichlorobenzoyl)-3H-spiro[2-benzofuran-1,4'-piperidin]-3-one

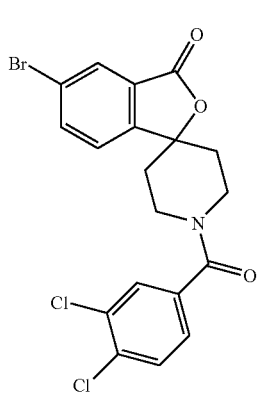

Amide coupling according to general procedure 2:
Amine: 5-bromo-3H-spiro[2-benzofuran-1,4'-piperidin]-3-one (described herein)
Acid: 3,4-Dichloro-benzoic acid
ES-MS m/e (%): 456.3 (M+H$^+$).
The synthesis of 5-bromo-3H-spiro[2-benzofuran-1,4'-piperidin]-3-one is described below (3):

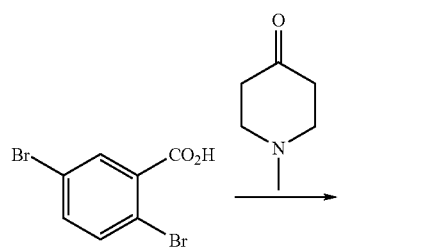

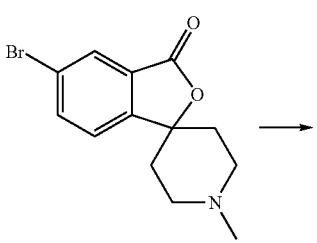

1

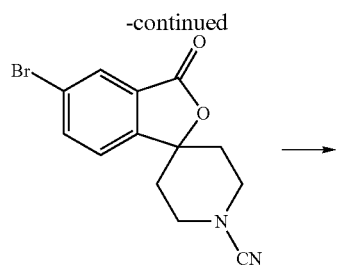

2

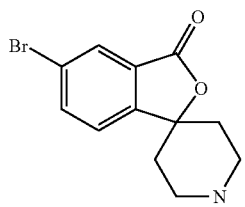

3

Preparation of 1: 1'-methyl-(5-bromo-3H-spiro[2-benzofuran-1,4'-piperidin]-3-one)

Butyllithium (97.2 ml of 1.47 M solution in hexane, 143 mmol) was added dropwise to a solution of 2,5-Dibromo-benzoic acid (20 g, 72 mmol) in dry THF (300 ml) at −78° C. over a period of 3.5 h under a nitrogen atmosphere. The reaction mixture was stirred at −78° C. for 2 h. A solution of N-methyl piperidone (11.31 g, 99 mmol) in hexane (40 mL) was added dropwise during 30 min to the reaction mixture at 78° C. The reaction mixture was allowed to come to room temperature and stirring was continued for overnight. The reaction mixture was added to a mixture of water (500 ml) and ether (300 mL). The aqueous layer was extracted with ether (5×150 mL) and acidified with concentrated HCl (to pH 2-3) and extracted with ether (2×150 ml).

The acidic solution was boiled for 1 h and then cooled to 0-5° C. and made alkaline (to pH 9-10) with aqueous NaOH. The cold solution was rapidly extracted with chloroform (5×300 mL). The combined chloroform extracts were washed with water (150 ml), dried over sodium sulfate and evaporated under reduced pressure. The residue was purified was purified by silica gel (100-200) column chromatography eluting with methanol in dichloromethane (0.5% to 2.5%) to afford 1 (4.2 g, 20%). $^1$H-NMR (400 MHz, CDCl3): δ 1.71 (d, J=14.2 Hz, 2H), 2.15-2.24 (m, 2H), 2.37 (s, 3H), 2.45-2.52 (m, 2H), 2.83-2.87 (m, 2H), 7.26 (d, J=8.25 Hz, 1H), 7.75 (dd, J=7.8, 1.7 Hz, 1H). $^{13}$C-NMR (100 MHz, CDCl3): δ 35.95, 46.05, 51.42, 84.00, 122.54, 122.97, 127.52, 128.64, 137.06, 152.24, 167.77.

Preparation of 2: 1'-cyano-(5-bromo-3H-spiro[2-benzofuran-1,4'-piperidin]-3-one)

A solution of 1 (3.0 g, 10 mmol) in choloroform (50 ml) was added dropwise to a stirred boiling solution of cyanogens bromide (12.16 g, 120 mmol) in chloroform (100 ml) under a nitrogen atmosphere and the resulting solution was refluxed for overnight. The reaction mixture was cooled and washed with 25 mL of 5% HCl and then with 20 ml of water. The organic layer was dried over sodium sulfate and evaporated under reduced pressure. The residue was purified by silica gel column chromatography (100-200) eluting with methanol in dichloromethane (0.5% to 1.0%) to get the pure product (1.6 g, 51%). ¹H-NMR (400 MHz, CDCl3): δ 1.72 (d, J=14.2 Hz, 2H), 2.24-2.32 (m, 2H), 3.37-3.59 (m, 4H), 7.32 (d, J=8.2 Hz, 1H), 7.83 (dd, J=8.0, 1.7 Hz, 1H), 8.03 (d, J=1.7 Hz, 1H).

Preparation of 3: (5-bromo-3H-spiro[2-benzofuran-1,4'-piperidin]-3-one)

A mixture of 2 (1.0 g, 3.2 mmol) and 20% HCl (12 ml) was heated under reflux under a nitrogen atmosphere for 6 h. The reaction mixture was cooled to 0-5° C. and pH was adjusted to 9-10 with aqueous NaOH solution and rapidly extracted with chloroform (3×50 ml). The combined extracts were washed with water, the organic layer was dried over sodium sulfate and evaporated under reduced pressure. The residue was washed with distilled hexane and dried under high vacuum to get the pure product (0.64 g, 70%). IR (KBr) 3333.84, 290.53, 283525, 2811.07, 2749.38, 1756.04, 1470.28, 1415.14, 1271.03, 1196.28, 1083.84, 929.07, 831.50, 792.35, 734.78, 691.24, 548.46, 534.50 cm⁻¹. ¹H-NMR (400 MHz, CDCl3): δ 1.66-1.72 (m, 2H), 2.02-2.09 (m, 2H), 3.07-3.18 (m, 4H), 7.29 (d, J=7.8 Hz, 1H), 7.77 (dd, J=7.8, 1.7 Hz, 1H), 7.99 (d, J=1.7 Hz, 1H). ¹³C-NMR (100 MHz, CDCl3): δ 6.33, 42.49, 85.23, 122.61, 122.93, 127.39, 128.64, 137.07, 152.44, 167.91. FIA-MS: 282.1 and 284.1; $C_{12}H_{12}^{79}BrNO_2$ [MH+] requires 282.1. mp: 162-163° C.

Example 11

1'-(3,4-Dichlorobenzoyl)-5-fluoro-3H-spiro[2-benzofuran-1,4'-piperidin]-3-one

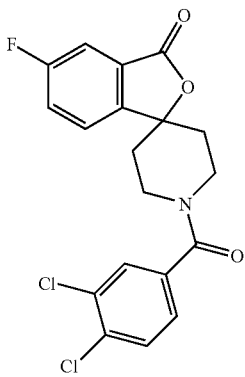

Amide coupling according to general procedure 2:
Amine: 5-fluoro-3H-spiro[2-benzofuran-1,4'-piperidin]-3-one (described in WO 2001014376)
Acid: 3,4-Dichloro-benzoic acid
ES-MS m/e (%): 394.3 (M+H⁺).

Example 12

1'-(3,4-Dichlorobenzoyl)-6-(2-hydroxyethoxy)-3H-spiro[2-benzofuran-1,4'-piperidin]-3-one

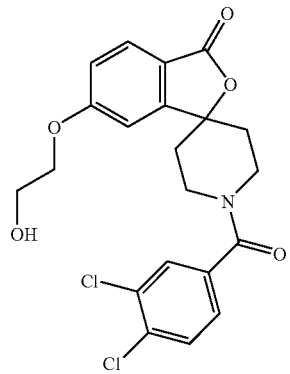

Amide coupling according to general procedure 2:
Amine: 6-(2-hydroxyethoxy)-3H-spiro[2-benzofuran-1,4'-piperidin]-3-one (described in WO 2001014376)
Acid: 3,4-Dichloro-benzoic acid
ES-MS m/e (%): 436.4 (M+H⁺).

Preparation of (6-(2-hydroxyethoxy)-3H-spiro[2-benzofuran-1,4'-piperidin]-3-one): 6

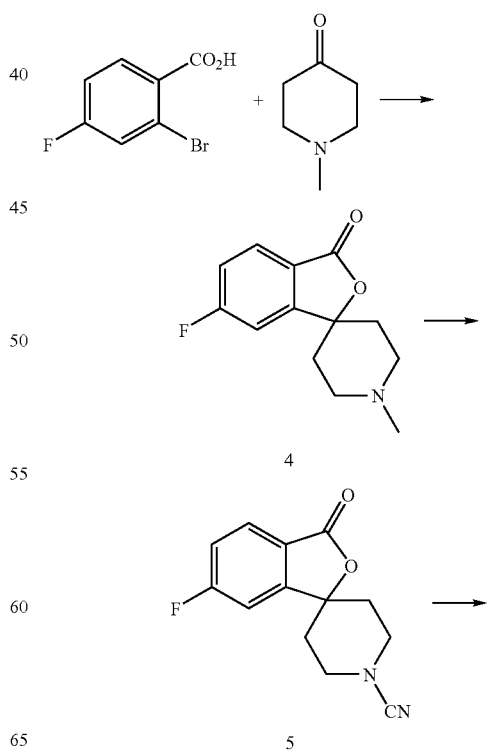

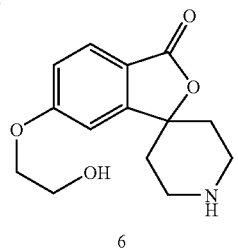

Preparation of 4: 1'-methyl-6-(2-fluoro-3H-spiro[2-benzofuran-1,4'-piperidin]-3-one To a solution of the substituted 2-bromo-4-fluoro-benzoic acid (10.9 g, 50 mmol) in dry THF (200 ml) at −78° C. n-butyllithium (1.6 M in hexanes) (100 mmol) was added drop wise (3 h) and the resulting solution was stirred for an additional 2 h at the same temperature. Freshly distilled N-methyl 4-piperidone 6 (7.91 g, 70 mmol) in dry hexane (25 ml) was added over 30 min at the same temperature. The mixture was then allowed to stir at rt and was finally added to ether (200 ml) and water (300 ml). The basic (aqueous) layer was extracted with ether (5×100 ml) and the aqueous layer was acidified with concentrated hydrochloric acid (pH 2-3) and extracted with ether. The aqueous solution was boiled for 1 h and was then cooled to 0-5° C. and made alkaline (pH 9-10) with cold aqueous sodium hydroxide. The cold solution was rapidly extracted with chloroform (5×200 ml). The combined chloroform extracts were washed with water, dried, concentrated to give light yellow solid which was purified over neutral alumina eluting with a gradient of 30-50% ethyl acetate-hexane to obtain 1.75 g (15%) of 9 as white solid. $^1$H-NMR (CDCl$_3$, 400 MHz): δ1.68-1.75 (m, 2H), 2.18-2.19 (m, 1H), 2.38 (s, 3H), 2.44-2.52 (m, 2H), 2.68-2.84 (m, 2H), 2.84-2.85 (m, 1H), 7.02-7.05 (m, 1H), 7.19-7.22 (m, 1H), 7.84-7.87 (m, 1H); FIA-MS: 236 (M+1).

Preparation of 5: 1'-cyano-6-(2-fluoro-3H-spiro[2-benzofuran-1,4'-piperidin]-3-one To a solution of the N-methylated lactone 9 (1.17 g, 5 mmol) in dry chloroform (10 ml) was added cyanogenbromide (60 mnol) and the resulting solution was refluxed for 36 h. The reaction mixture was extracted with 5% HCl (5 ml) and then with water (2.5 ml). The chloroform solution was dried (anhydrous MgSO4) and concentrated to give a pale yellow solid which was chromatographed over SiO2 eluting with 1% MeOH—CH2Cl2 to give 858 mg (70%) 5 as white solid. $^1$H-NMR (CDCl$_3$, 400 MHz): δ1.72-1.76 (m, 2H), 2.22-2.30 (m, 1H), 3.48-3.60 (m, 4H), 7.09-7.11 (m, 1H), 7.11-7.28 (m, 1H), 7.89-7.92 (m, 1H); IR (KBr): 3492, 3043, 2216, 1760, 1602, 1478 cm−1.

Preparation of 6: 6-(2-hydroxyethoxy)-3H-spiro[2-benzofuran-1,4'-piperidin]-3-one)

N-cyano lactone 5 (1.23 g, 5 mmol) was heated with ethylene glycol (5 ml) and sodium hydroxide (0.82 g, 20.5 mmol) for 15-20 min at 130° C. Most of the ethylene glycol was removed by distillation under high vacuum. The residual reaction mixture was diluted with water and extracted repeatedly with chloroform. The combined organics was dried and concentrated to give a semi solid material which was purified over Al2O3 column upon elution with 5-7% MeOH/CH$_2$Cl$_2$ containing NH3 (aqueous) to yield 789 mg (60%) of CRI 1072 as pale yellow solid. $^1$H-NMR (d6-DMSO, 400 MHz): δ1.47-1.50 (m, 2H), 2.03-2.10 (m, 2H), 2.79-2.85 (m, 2H), 2.95-2.97 (m, 2H), 3.73-3.76 (m, 2H), 4.12-4.14 (m, 2H), 7.09 (d, J=8.4 Hz, 1H), 7.20 (s, 1H), 7.69 (d, J=8.4 Hz, 1H); $^{13}$C-NMR (d6-DMSO, 100 MHz): δ35.9, 42.3, 59.3, 70.4, 84.6, 106.4, 116.6, 117.0, 126.8, 156.9, 163.9, 168.5; FIA-MS: 264.3 (M+1).

Example 13

1'-(2,3-Dichlorobenzoyl)-3H-spiro[2-benzofuran-1,4'-piperidin]-3-one

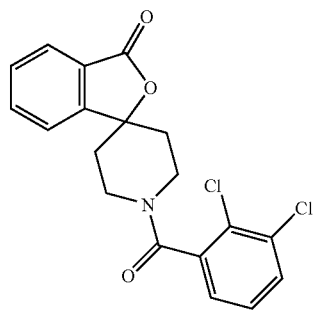

Amide coupling according to general procedure 2:

Amine: 3H-spiro[2-benzofuran-1,4'-piperidin]-3-one (described in Journal of Organic Chemistry (1976), 41(15), 2628-33)

Acid: 2,3-Dichloro-benzoic acid

ES-MS m/e (%): 376.4 (M+H$^+$).

Example 14

1'-(2,3-Dichlorobenzoyl)-6-methoxy-3H-spiro[2-benzofuran-1,4'-piperidin]-3-one

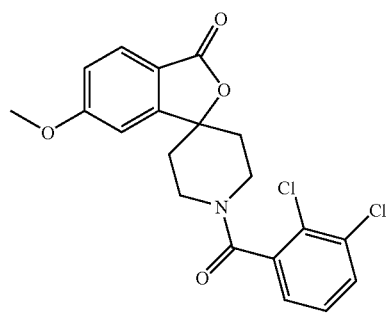

Amide coupling according to general procedure 2:

Amine: 6-methoxy-3H-spiro[2-benzofuran-1,4'-piperidin]-3-one (described in EP 722941)

Acid: 2,3-Dichloro-benzoic acid

ES-MS m/e (%): 406.4 (M+H$^+$).

Example 15

6-Chloro-1'-(2,3-dichlorobenzoyl)-3H-spiro[2-benzofuran-1,4'-piperidin]-3-one

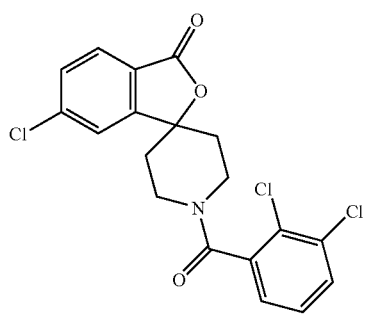

Amide coupling according to general procedure 2:
Amine: 6-chloro-3H-spiro[2-benzofuran-1,4'-piperidin]-3-one (described in EP 722941)
Acid: 2,3-Dichloro-benzoic acid
ES-MS m/e (%): 410.2 (M+H$^+$).

Example 16

1'-(2,3-Dichlorobenzoyl)-5-methoxy-3H-spiro[2-benzofuran-1,4'-piperidin]-3-one

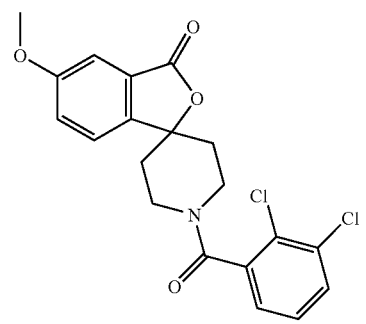

Amide coupling according to general procedure 2:
Amine: 5-methoxy-3H-spiro[2-benzofuran-1,4'-piperidin]-3-one (described in EP 722941)
Acid: 2,3-Dichloro-benzoic acid
ES-MS m/e (%): 406.4 (M+H$^+$).

Example 17

1'-(2,3-Dichlorobenzoyl)-5-fluoro-3H-spiro[2-benzofuran-1,4'-piperidin]-3-one

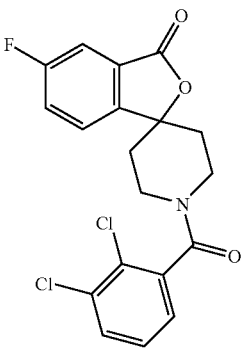

Amide coupling according to general procedure 2:
Amine: 5-fluoro-3H-spiro[2-benzofuran-1,4'-piperidin]-3-one (described in WO 2001014376)
Acid: 2,3-Dichloro-benzoic acid
ES-MS m/e (%): 394.3 (M+H$^+$).

Example 18

1'-(2,3-Dichlorobenzoyl)-6-(2-hydroxyethoxy)-3H-spiro[2-benzofuran-1,4'-piperidin]-3-one

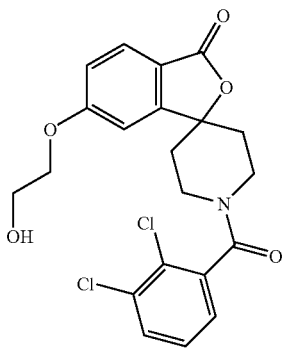

Amide coupling according to general procedure 2:
Amine: 6-(2-hydroxyethoxy)-3H-spiro[2-benzofuran-1,4'-piperidin]-3-one (described herein)
Acid: 2,3-Dichloro-benzoic acid
ES-MS m/e (%): 436.4 (M+H$^+$).

Example 19

1'-[(5-Chloro-1H-indazol-7-yl)carbonyl]-3H-spiro[2-benzofuran-1,4'-piperidin]-3-one

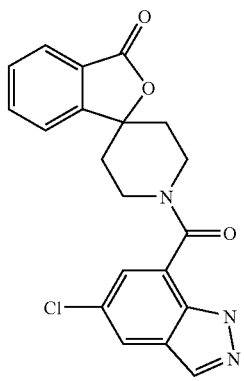

Amide coupling according to general procedure 2:

Amine: 3H-spiro[2-benzofuran-1,4'-piperidin]-3-one (described in Journal of Organic Chemistry (1976), 41(15), 2628-33)

Acid: 5-Chloro-1H-indazole-7-carboxylic acid (described in WO 2006013048)

ES-MS m/e (%): 382.4 (M+H$^+$).

Example 20

1'-[(5-Chloro-1H-indazol-7-yl)carbonyl]-6-methoxy-3H-spiro[2-benzofuran-1,4'-piperidin]-3-one

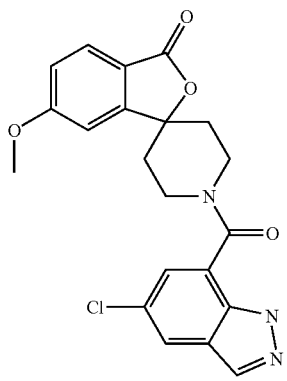

Amide coupling according to general procedure 2:

Amine: 6-methoxy-3H-spiro[2-benzofuran-1,4'-piperidin]-3-one (described in EP 722941)

Acid: 5-Chloro-1H-indazole-7-carboxylic acid (described in WO 2006013048)

ES-MS m/e (%): 412.4 (M+H$^+$).

Example 21

1'-(1-Naphthoyl)-3H-spiro[2-benzofuran-1,4'-piperidine]

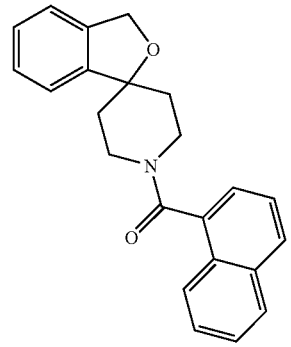

Amide coupling according to general procedure 2:

Amine: 3H-spiro[2-benzofuran-1,4'-piperidine] (CAS 38309-60-3)

Acid: Naphthalene-1-carboxylic acid

ES-MS m/e (%): 344.4 (M+H$^+$).

Example 22

4-Fluoro-1'-(1-naphthoyl)-3H-spiro[2-benzofuran-1,4'-piperidine]

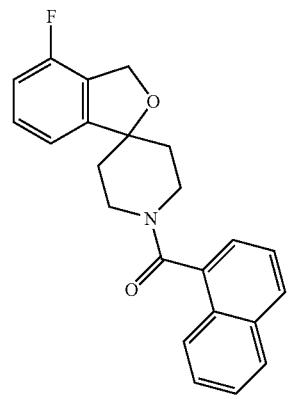

Amide coupling according to general procedure 2:

Amine: 4-fluoro-3H-spiro[2-benzofuran-1,4'-piperidine] (prepared according to Journal of Medicinal Chemistry (1995), 38(11), 2009-17)

Acid: Naphthalene-1-carboxylic acid

ES-MS m/e (%): 362.3 (M+H$^+$).

Example 23

1'-(2-Ethoxy-1-naphthoyl)-4-fluoro-3H-spiro[2-benzofuran-1,4'-piperidine]

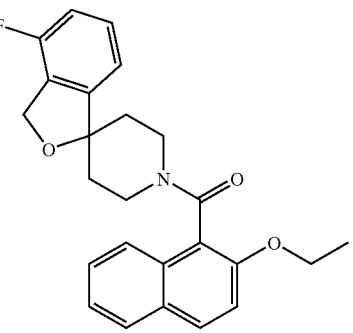

Amide coupling according to general procedure 2:

Amine: 4-fluoro-3H-spiro[2-benzofuran-1,4'-piperidine] (prepared according to Journal of Medicinal Chemistry (1995), 38(11), 2009-17)

Acid: 2-Ethoxynaphthalene-1-carboxylic acid (CAS 2224-00-2)

ES-MS m/e (%): 406.5 (M+H$^+$).

Example 24

1'-(2-Ethoxy-1-naphthoyl)-3H-spiro[2-benzofuran-1,4'-piperidine]

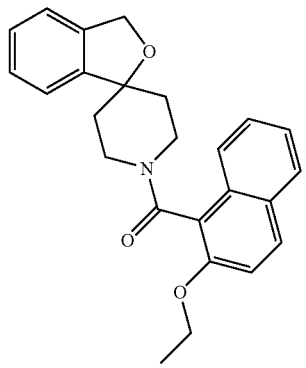

Amide coupling according to general procedure 2:

Amine: 3H-spiro[2-benzofuran-1,4'-piperidine] (CAS 38309-60-3)

Acid: 2-Ethoxynaphthalene-1-carboxylic acid (CA 2224-00-2)

ES-MS m/e (%): 388.3 (M+H$^+$).

Example 25

1'-(4-tert-Butylbenzoyl)-3H-spiro[2-benzofuran-1,4'-piperidine]

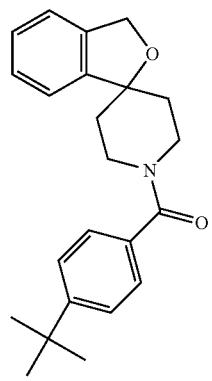

Amide coupling according to general procedure 1:

Amine: 3H-spiro[2-benzofuran-1,4'-piperidine] (CAS 38309-60-3)

Acid: 4-tert-Butyl-benzoyl chloride

ES-MS m/e (%): 350.5 (M+H$^+$).

Example 26

1'-[(2,2-Difluoro-1,3-benzodioxol-4-yl)carbonyl]-3H-spiro[2-benzofuran-1,4'-piperidine]

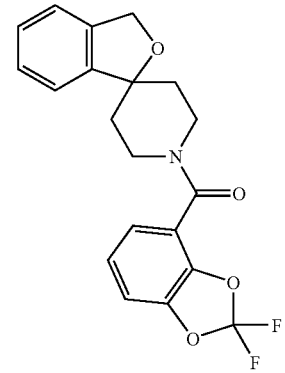

Amide coupling according to general procedure 1:

Amine: 3H-spiro[2-benzofuran-1,4'-piperidine] (CAS 38309-60-3)

Acid: 2,2-Difluoro-benzo[1,3]dioxole-4-carbonyl chloride (CAS 143096-86-0)

ES-MS m/e (%): 374.4 (M+H$^+$).

Example 27

1'-[(5-Methoxy-1H-indol-7-yl)carbonyl]-3H-spiro[2-benzofuran-1,4'-piperidine]

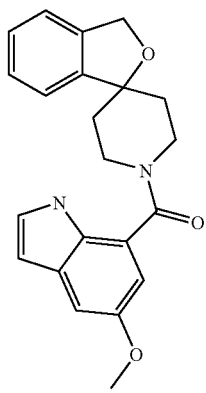

Amide coupling according to general procedure 2:
Amine: 3H-spiro[2-benzofuran-1,4'-piperidine] (CAS 38309-60-3)
Acid: 5-Methoxy-1H-indole-7-carboxylic acid (prepared herein)
ES-MS m/e (%): 363.5 (M+H$^+$).

Preparation of 5-Methoxy-1H-indole-7-carboxylic acid

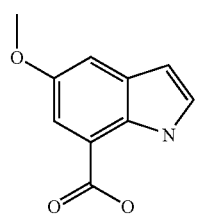

A solution of 7-Bromo-5-methoxy-1H-indole (described in WO 2002028861) in THF was treated with 2 eq. of a solution of n-BuLi in n-hexane (1.6M) at 5° and after 30 min at this temperature was cooled to −75°. Dry ice (excess) was added and after 15 mins the mixture was quenched with H$_2$O and washed with EtOAc. After acidification of the aqueous layer and extraction into CH$_2$Cl$_2$, evaporation gave the desired product.
ES-MS m/e (%): 192.1 (M+H$^+$).

Example 28

1'-(1H-Benzimidazol-7-ylcarbonyl)-3H-spiro[2-benzofuran-1,4'-piperidine]

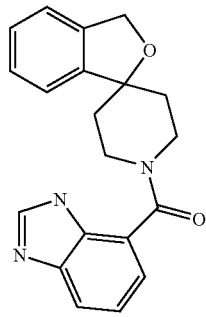

Amide coupling according to general procedure 2:
Amine: 3H-spiro[2-benzofuran-1,4'-piperidine] (CAS 38309-60-3)
Acid: 3H-Benzoimidazole-4-carboxylic acid (CAS 46006-36-4)
ES-MS m/e (%): 334.4 (M+H$^+$).

Example 29

1'-(1H-Indol-7-ylcarbonyl)-3H-spiro[2-benzofuran-1,4'-piperidine]

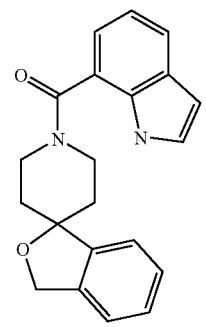

Amide coupling according to general procedure 2:
Amine: 3H-spiro[2-benzofuran-1,4'-piperidine] (CAS 38309-60-3)
Acid: 1H-Indole-7-carboxylic acid (CAS 1670-83-3)
ES-MS m/e (%): 333.5 (M+H$^+$).

Example 30

1'-(1,3-Benzodioxol-4-ylcarbonyl)-3H-spiro[2-benzofuran-1,4'-piperidine]

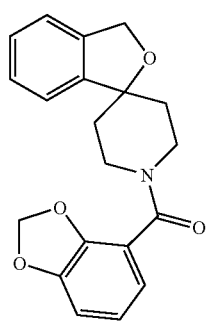

Amide coupling according to general procedure 2:
Amine: 3H-spiro[2-benzofuran-1,4'-piperidine] (CAS 38309-60-3)
Acid: Benzo[1,3]dioxole-4-carboxylic acid (CAS 5768-39-8)
ES-MS m/e (%): 338.4 (M+H⁺).

Example 31

3,3-Dimethyl-6-(1'H,3H-spiro[2-benzofuran-1,4'-piperidin]-1'-ylcarbonyl)-1,3-dihydro-2H-indol-2-one

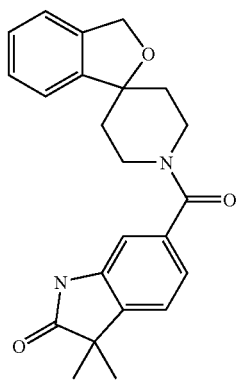

Amide coupling according to general procedure 2:
Amine: 3H-spiro[2-benzofuran-1,4'-piperidine] (CAS 38309-60-3)
Acid: 3,3-Dimethyl-2-oxo-2,3-dihydro-1H-indole-6-carboxylic acid (described in EP 344634)
ES-MS m/e (%): 377.5 (M+H⁺).

Example 32

5-Bromo-1'-(4-tert-butylbenzoyl)spiro[indole-3,4'-piperidin]-2(1H)-one

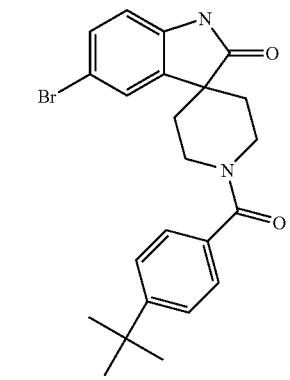

Amide coupling according to general procedure 2:
Amine: 5-bromo-spiro[indole-3,4'-piperidin]-2(1H)-one (preparation described herein)
Acid: 4-tert-Butyl-benzoic acid
ES-MS m/e (%): 441.5 (M+H⁺).

5-Bromo-spiro[indole-3,4'-piperidin]-2(1H)-one

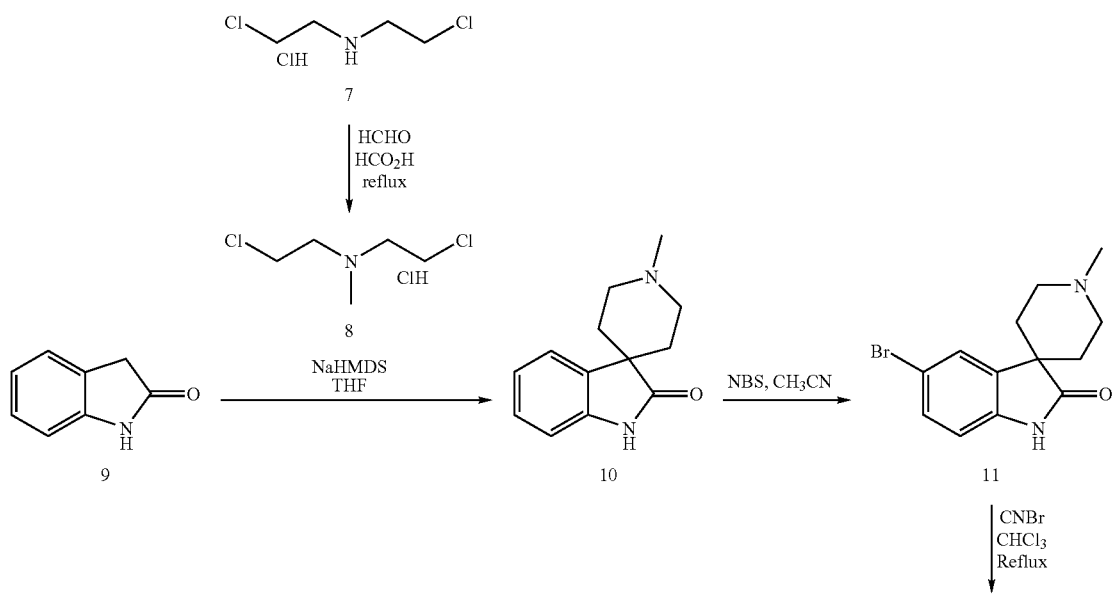

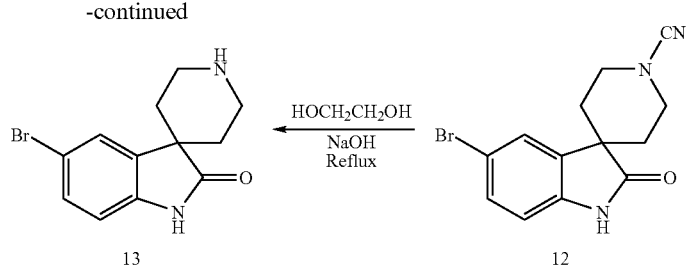

1,5-Dichloro-3-methyl-3-azapentane, hydrochloride 8

Formic acid (10.0 g; 0.2 mol) and 37% formaldehyde (20 ml) were mixed in a 250 ml round-bottom flask equipped with reflux condenser. 1,5-Dichloro-3-azapentane, hydrochloride (17.0 g; 0.1 mol) was added and the solution was heated with magnetic stirring at 100° C. After 3 h the temperature was increased to 120° C. for 20 min and finally allowed to cool to room temperature before the solvent was evaporated in vacuo to afford 8 as white solid in quantitative yield. $^1$HNMR (CD$_3$OD, 400 MHz) δ 3.0 (s, 3H); 3.45 (br s, 2H); 3.62 (br s, 2H); 4.07 (br s, 4H).

1'-(Methyl)spiro[indole-3,4'-piperidin]-2(1H)-one 10

A solution of oxindole 9 (6.25 g, 47 mmol) in THF (500 ml) was cooled to −78° C. and to it a solution of sodium hexamethyldisilazide (43 g, 235 mmol) in THF (300 ml) was added drop wise under N$_2$ atmosphere. After stirring at −78° C. for 45 min, N-methylbis(2-chloromethyl)amine hydrochloride (9 g, 47 mmol) was added, as a solid. The reaction mixture was stirred at −78° C. for 1 h and at room temperature for 24 h. After quenching with H$_2$O (90 ml), the mixture was extracted with ethyl acetate (3×100 ml). The organic extracts were washed with brine (25 ml), dried and the solvent removed in vacuo. Silica gel chromatography (5-50% MeOH/CH$_2$Cl$_2$, gradient) gave 6 g (57%) of 10 as a solid. $^1$HNMR (CD$_3$OD, 400 MHz) δ 1.84 (m, 2H); 2.51 (m, 2H); 2.62 (s, 3H); 3.02 (m, 2H); 3.37 (m, 2H); 6.82 (d, 1H, J=7.68 Hz); 6.94 (t, 1H, J=7.58 Hz); 7.12 (t, 1H, J=7.7 Hz); 7.26 (d, 1H, J=9 Hz); 9.27 (br s, 1H).

5-bromo-1'-(methyl)spiro[indole-3,4'-piperidin]-2(1H)-one (11)

A solution of 1'-(methyl)spiro[indole-3,4'-piperidin]-2(1H)-one (6.3 g, 29.1 mmol) in CH$_3$CN (100 ml) and MeOH (5 ml) was cooled to −5° C. and NBS (7.8 g, 44 mmol) was slowly added with stirring. The reaction mixture was stirred for 3.5 h at 0° C. Solvent was removed by vacuo. The residue was purified by silica gel chromatography (2-20% MeOH/CH$_2$Cl$_2$) to give 6 g as a solid. The solid compound was dissolved in ethyl acetate (600 ml) and washed with saturated aqueous NaHCO$_3$ solution, dried (Na$_2$SO$_4$). Evaporation of the solvent in vacuo gave 4.2 g (47%) of 11. $^1$HNMR (CD$_3$OD, 400 MHz) δ 7.51 (d, J=1.8 Hz, 1H), 7.35 (dd, J=1.9 and 8.2 Hz, 1H), 6.81 (d, J=8.2 Hz, 1H), 2.93 (m, 2H), 2.67 (m, 2H), 2.41 (s, 3H), 1.86 (m, 4H).

5-bromo-1'-(cyano)spiro[indole-3,4'-piperidin]-2(1H)-one (12)

5-bromo-1'-(methyl)spiro[indole-3,4'-piperidin]-2(1H)-one 11 (4.6 g, 15.6 mmol) was dissolved in chloroform (700 ml) and treated with CNBr (22 g, 209.5 mmol) at room temperature. The mixture was heated to reflux for 24 h. The reaction mixture was cooled, diluted with methylene chloride (300 ml) and washed with 10% aqueous K$_2$CO$_3$ solution (2×100 ml). After the mixture was dried (Na$_2$SO$_4$) and concentrated, the residue was purified by silica gel chromatography (0-5% MeOH/CH$_2$Cl$_2$) to gave 7 as a solid 3.9 g (82%). $^1$HNMR (CDCl$_3$, 400 MHz) δ 7.52 (d, J=1.8 Hz, 1H), 7.37 (dd, J=1.8 and 8.2 Hz, 1H), 6.82 (d, J=8.2 Hz, 1H), 3.83 (m, 2H), 3.41 (m, 2H), 2.00 (m, 2H), 1.86 (m, 2H).

5-bromo-spiro[indole-3,4'-piperidin]-2(1H)-one (13)

5-Bromo-1,2-dihydro-2-oxospiro[3H-indole-3,4'-piperidine]-1'-cyano 12 (3.3 g, 10.8 mmol) was suspended in ethylene glycol (10 ml). The mixture was treated in NaOH (1.8 g, 45 mmol) and heated to 130° C. for 15 min. It was diluted with methylene chloride (500 ml) and washed with 10% aqueous K$_2$CO$_3$ (2×100 m). The organic layer was dried (Na$_2$SO$_4$) and concentrated and residue purified by silica gel chromatography (30% MeOH/CH$_2$Cl$_2$) to gave 13 as a light ceramic white solid 1.8 g (60%), mp 256-258° C. $^1$HNMR (DMSO-d$_6$, 400 MHz) δ 10.6 (br s, 1H, NH), 7.57 (d, J=1.84 Hz, 1H), 7.36 (d, J=8.2 Hz, 1H), 6.79 (d, J=8.2 Hz, 1H), 4.05 (br s, 1H, NH), 3.06 (m, 2H), 2.84 (m, 2H), 1.64 (m, 2H), 1.55 (m, 2H), $^{13}$C NMR (DMSO-d$_6$, 100 MHz) δ 180.93, 140.64, 137.98, 130.42, 126.75, 113.20, 111.45, 46.24, 40.92, 32.94. Anal. Calcd for C$_{12}$H$_{13}$BrN$_2$O: C, 51.26; H, 4.66; N, 9.9. Found: C, 50.87; H, 4.91; N, 9.67.

Example 33

5-Bromo-1'-(2-naphthoyl)spiro[indole-3,4'-piperidin]-2(1H)-one

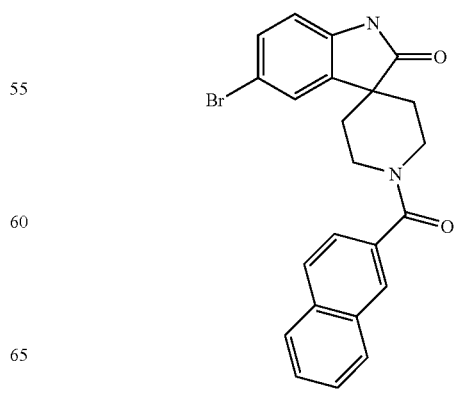

Amide coupling according to general procedure 2:
Amine: 5-bromo-spiro[indole-3,4'-piperidin]-2(1H)-one (preparation described herein)
Acid: Naphthalene-2-carboxylic acid
ES-MS m/e (%): 435.4 (M+H$^+$).

Example 34

1'-(4-Chlorobenzoyl)-4-methylspiro[indole-3,4'-piperidin]-2(1H)-one

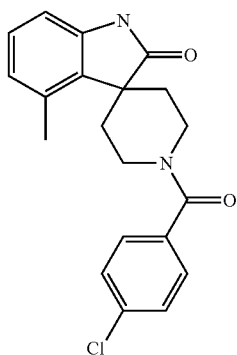

Amide coupling according to general procedure 2:
Amine: 4-methylspiro[indole-3,4'-piperidin]-2(1H)-one (preparation in analogy to 5-bromo-spiro[indole-3,4'-piperidin]-2(1H)-one starting from 1,5-Dichloro-3-methyl-3-azapentane, hydrochloride
Acid: 4-Chloro-benzoic acid
ES-MS m/e (%): 355.4 (M+H$^+$).

Example 35

1'-(3,4-Dichlorobenzoyl)spiro[1-benzofuran-3,4'-piperidine]

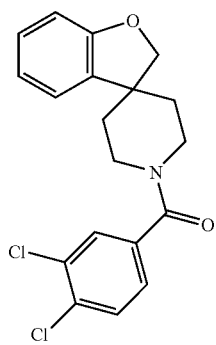

Amide coupling according to general procedure 2:
Amine: Spiro[1-benzofuran-3,4'-piperidine] (CAS 38309-60-3)
Acid: 3,4-Dichloro-benzoic acid
ES-MS m/e (%): 362.4 (M+H$^+$).

Example 36

1'-(2-Naphthoyl)spiro[indene-1,4'-piperidine]

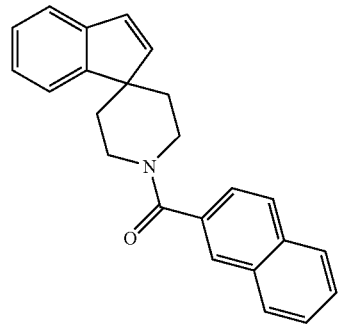

Amide coupling according to general procedure 2:
Amine: Spiro[indene-1,4'-piperidine] (CAS 33042-66-9)
Acid: Naphthalene-2-carboxylic acid
ES-MS m/e (%): 340.5 (M+H$^+$).

Example 37

1'-(4-tert-Butylbenzoyl)spiro[indene-1,4'-piperidine]

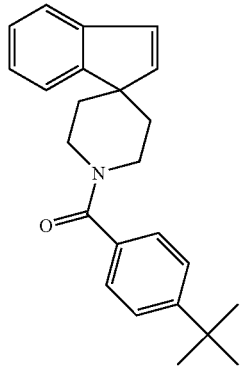

Amide coupling according to general procedure 2:
Amine: Spiro[indene-1,4'-piperidine] (CAS 33042-66-9)
Acid: 4-tert-Butyl-benzoic acid
ES-MS m/e (%): 346.5 (M+H$^+$).

Example 38

1'-[(2,2-Difluoro-1,3-benzodioxol-4-yl)carbonyl]spiro[indene-1,4'-piperidine]

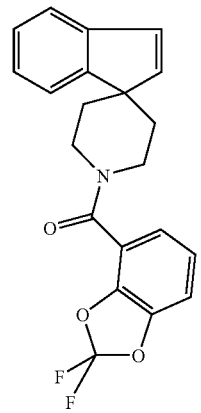

Amide coupling according to general procedure 2:
Amine: Spiro[indene-1,4'-piperidine] (CAS 33042-66-9)
Acid: 2,2-Difluoro-benzo[1,3]dioxole-4-carbonyl chloride (CAS 143096-86-0)
ES-MS m/e (%): 370.4 (M+H$^+$).

Example 39

1'-(3,4-Dichlorobenzoyl)spiro[indene-1,4'-piperidine]

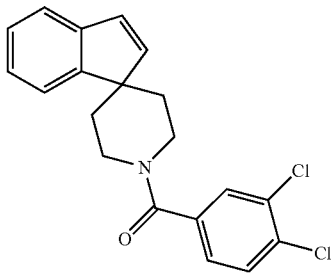

Amide coupling according to general procedure 2:
Amine: Spiro[indene-1,4'-piperidine] (CAS 33042-66-9)
Acid: 3,4-Dichloro-benzoic acid
ES-MS m/e (%): 358.4 (M+H$^+$).

Example 40

1'-(2,3-Dichlorobenzoyl)spiro[indene-1,4'-piperidine]

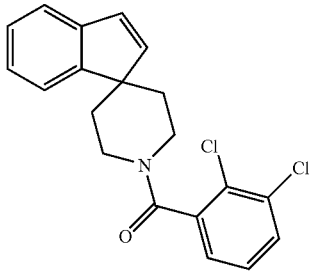

Amide coupling according to general procedure 2:
Amine: Spiro[indene-1,4'-piperidine] (CAS 33042-66-9)
Acid: 2,3-Dichloro-benzoic acid
ES-MS m/e (%): 358.4 (M+H$^+$).

Example 41

1'-[(5-Chloro-1H-indazol-7-yl)carbonyl]spiro[indene-1,4'-piperidine]

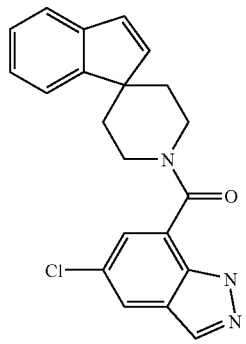

Amide coupling according to general procedure 2:
Amine: Spiro[indene-1,4'-piperidine] (CAS 33042-66-9)
Acid: 5-Chloro-1H-indazole-7-carboxylic acid (described in WO 2006013048)
ES-MS m/e (%): 364.4 (M+H$^+$).

Example 42

1'-(3,4-Dichlorobenzoyl)-2,3-dihydrospiro[indene-1,4'-piperidine]

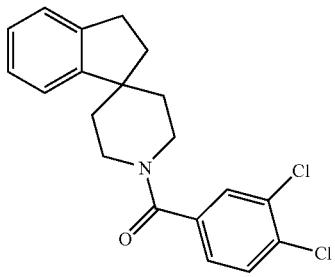

Amide coupling according to general procedure 2:
Amine: 2,3-Dihydrospiro[indene-1,4'-piperidine] (CAS 428-38-6)
Acid: 3,4-Dichloro-benzoic acid
ES-MS m/e (%): 360.4 (M+H$^+$).

Example 43

1'-(2,3-Dichlorobenzoyl)-2,3-dihydrospiro[indene-1,4'-piperidine]

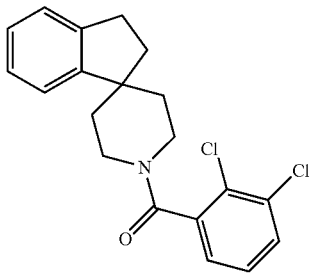

Amide coupling according to general procedure 2:
Amine: 2,3-Dihydrospiro[indene-1,4'-piperidine] (CAS 428-38-6)
Acid: 2,3-Dichloro-benzoic acid
ES-MS m/e (%): 360.4 (M+H$^+$).

The invention claimed is:
1. A compound of formula (I)

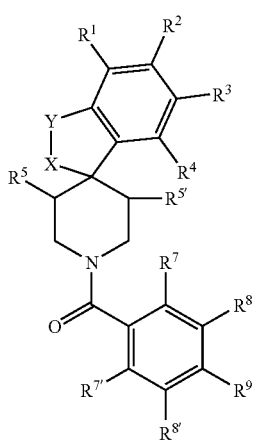

wherein
X is O and Y is C=O,
X is O and Y is CH$_2$,
X is CH$_2$ and Y is O, or
X is C=O and Y is O;
R$^1$, R$^2$, R$^3$ and R$^4$ are each independently
hydrogen,
halo,
C$_{1-6}$-alkyl, optionally substituted by OH,
halo-C$_{1-6}$-alkyl,
C$_{1-6}$-alkoxy, optionally substituted by OH, or
halo-C$_{1-6}$-alkoxy;
R$^5$ and R$^{5'}$ are each independently hydrogen or methyl;
R$^7$, R$^{7'}$ R$^8$, R$^{8'}$, and R$^9$ are each independently selected from
hydrogen,
halo,
C$_{1-6}$-alkyl,
halo-C$_{1-6}$-alkoxy,
nitro, and
cyano, or R$^7$ and R$^8$, R$^{7'}$ and R$^{8'}$, R$^8$ and R$^9$, or R$^{8'}$ and R$^9$ are bound together to form a ring with the phenyl moiety, wherein
—R$^7$—R$^8$— or —R$^{7'}$—R$^{8'}$— is
—N(R$^{10}$)—N=CH—, or —CH=N—N(R$^{10}$)—,
wherein R$^{10}$ is hydrogen or C$_{1-6}$-alkyl,
—N(R$^{11}$)—CH=CH—, or —CH=CH—N(R$^{12}$)—,
wherein R$^{11}$ is hydrogen or C$_{1-6}$-alkyl,
—C(R$^{12}$)=C(R$^{13}$)—C(R$^{14}$)=C(R$^{15}$)—,
wherein R$^{12}$, R$^{13}$, R$^{14}$, and R$^{15}$ are each independently selected from hydrogen, halo, halo-C$_{1-6}$-alkyl, C$_{1-6}$-alkyl, C$_{1-6}$-alkoxy,
halo-C$_{1-6}$-alkoxy, nitro, and cyano,
—O—(CR$^{16}$R$^{16'}$)$_n$—O—,
wherein n is 1 or 2, and R$^{16}$ and R$^{16'}$ are each independently hydrogen, halo or C$_{1-6}$-alkyl,
—N(R$^{17}$)—CH=N—, or —N=CH—N(R$^{17}$)—,
wherein R$^{17}$ is hydrogen or C$_{1-6}$-alkyl, or
—N(R$^{18}$)—C(O)—CH$_2$— or —CH$_2$—C(O)—N(R$^{18}$)—,
wherein R$^{18}$ is hydrogen or C$_{1-6}$-alkyl,
or a pharmaceutically acceptable salt thereof.

2. The compound of claim 1 having formula I-a

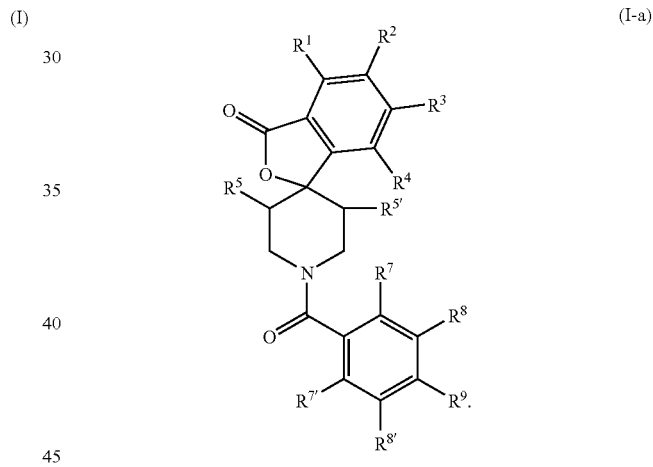

3. The compound of claim 1 having formula I-b

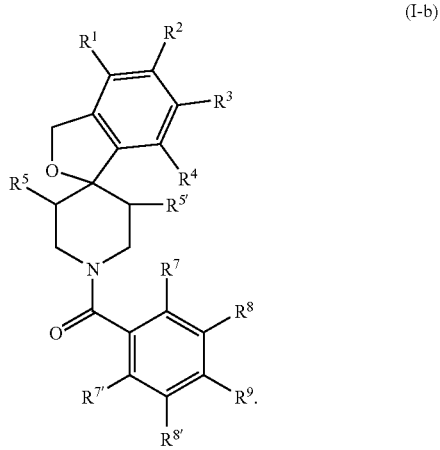

4. The compound of claim 1 having formula I-d

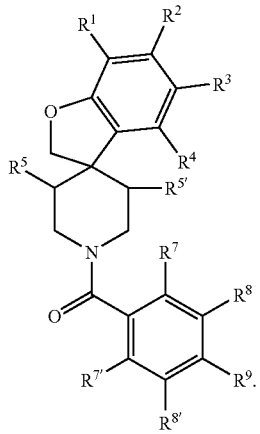

(I-d)

5. The compound of claim 1 having formula I-g

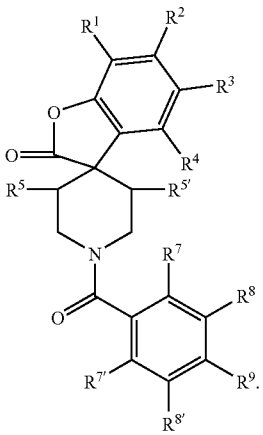

(I-g)

6. The compound of claim 1, wherein
$R^1$, $R^2$, $R^3$ and $R^4$ are each independently
hydrogen,
halo,
$C_{1-6}$-alkyl, or
$C_{1-6}$-alkoxy, optionally substituted by OH.

7. The compound of claim 1 wherein $R^1$ is hydrogen or halo.

8. The compound of claim 1, wherein $R^2$ is hydrogen, halo, or $C_{1-6}$-alkoxy.

9. The compound of claim 1, wherein $R^3$ is hydrogen, halo, or $C_{1-6}$-alkoxy, optionally substituted by OH.

10. The compound of claim 1, wherein $R^4$ is hydrogen or $C_{1-6}$-alkyl.

11. The compound of claim 1, wherein $R^1$, $R^2$, $R^3$, and $R^4$ are hydrogen.

12. The compound of claim 1, wherein $R^1$, $R^2$, $R^3$, and $R^4$, are each independently $C_{1-6}$-alkyl or $C_{1-6}$-alkoxy, optionally substituted by OH.

13. The compound of claim 1, wherein $R^5$ and $R^{5'}$ are both hydrogen or wherein $R^5$ and $R^{5'}$ are both $C_{1-6}$-alkyl.

14. The compound of claim 1, wherein $R^6$ is hydrogen or $C_{1-6}$-alkyl.

15. The compound of claim 1, wherein $R^7$ and $R^{7'}$ are both hydrogen.

16. The compound of claim 1, wherein $R^7$ and $R^{7'}$ are each independently hydrogen or halo.

17. The compound of claim 1, wherein one of $R^7$ and $R^{7'}$ is hydrogen and the other is halo, $C_{1-6}$-alkyl, halo-$C_{1-6}$-alkoxy, nitro, or cyano.

18. The compound of claim 1, wherein $R^8$ and $R^{8'}$ are each independently hydrogen or halo.

19. The compound of claim 1, wherein
$R^7$ and $R^8$ or $R^{7'}$ and $R^{8'}$ are bound together to form a ring with the phenyl moiety, wherein
—$R^7$—$R^8$— or —$R^{7'}$—$R^{8'}$— is
—N($R^{10}$)—N=CH— or —CH=N—N($R^{10}$)—,
wherein $R^{10}$ is hydrogen or $C_{1-6}$-alkyl,
—N($R^{11}$)—CH=CH— or —CH=CH—N($R^{12}$)—,
wherein $R^{11}$ is hydrogen or $C_{1-6}$-alkyl,
—C($R^{12}$)=C($R^{13}$)—C($R^{14}$)=C($R^{15}$)—,
wherein $R^{12}$, $R^{13}$, $R^{14}$, and $R^{15}$ are each independently selected from hydrogen, halo, halo-$C_{1-6}$-alkyl, $C_{1-6}$-alkoxy,
halo-$C_{1-6}$-alkoxy, nitro, and cyano,
—O—(C$R^{16}R^{16'}$)$_n$—O—,
wherein n is 1 or 2, and $R^{16}$ and $R^{16'}$ are each independently hydrogen, halo or $C_{1-6}$-alkyl, or
—N($R^{17}$)—CH=N— or —N=CH—N($R^{17}$)—,
wherein $R^{17}$ is hydrogen or $C_{1-6}$-alkyl.

20. The compound of claim 1, wherein $R^9$ is hydrogen, halo, or
$C_{1-6}$-alkyl.

21. The compound of claim 1, wherein
$R^8$ and $R^9$ or $R^{8'}$ and $R^9$ are bound together to form a ring with the phenyl moiety, wherein
—$R^8$—$R^9$— or —$R^{8'}$—$R^9$— is
—C($R^{12}$)=C($R^{13}$)—C($R^{14}$)=C($R^{15}$)—,
wherein $R^{12}$, $R^{13}$, $R^{14}$, and $R^{15}$ are each independently selected from hydrogen, halo, halo-$C_{1-6}$-alkyl, $C_{1-6}$-alkyl, $C_{1-6}$-alkoxy,
halo-$C_{1-6}$-alkoxy, nitro, and cyano,
—N($R^{18}$)—C(O)—CH$_2$— or —CH$_2$—C(O)—N($R^{18}$)—,
wherein $R^{18}$ is hydrogen or $C_{1-6}$-alkyl.

22. The compound of claim 1, wherein $R^7$ and $R^8$ are bond together to form a ring with the phenyl moiety.

23. The compound of claim 1, wherein $R^{7'}$ and $R^{8'}$ are bound together to form a ring with the phenyl moiety.

24. The compound of claim 1, selected from the group consisting of
6-Methoxy-1'-(2-naphthoyl)-3H-spiro[2-benzofuran-1,4'-piperidin]-3-one;
1'-(4-tert-Butylbenzoyl)-6-chloro-3H-spiro[2-benzofuran-1,4'-piperidin]-3-one;
Rac-(1R,3'S)-1'-(4-tert-butylbenzoyl)-3'-methyl-3H-spiro[2-benzofuran-1,4'-piperidin]-3-one;
1'-(4-tert-Butylbenzoyl)-3H-spiro[2-benzofuran-1,4'-piperidin]-3-one;
5-Methoxy-1'-(2-naphthoyl)-3H-spiro[2-benzofuran-1,4'-piperidin]-3-one;
1'-(3,4-Dichlorobenzoyl)-3H-spiro[2-benzofuran-1,4'-piperidin]-3-one;
1'-(3,4-Dichlorobenzoyl)-6-methoxy-3H-spiro[2-benzofuran-1,4'-piperidin]-3-one;
6-Chloro-1'-(3,4-dichlorobenzoyl)-3H-spiro[2-benzofuran-1,4'-piperidin]-3-one;
1'-(3,4-Dichlorobenzoyl)-5-methoxy-3H-spiro[2-benzofuran-1,4'-piperidin]-3-one;
5-Bromo-1'-(3,4-dichlorobenzoyl)-3H-spiro[2-benzofuran-1,4'-piperidin]-3-one;

1'-(3,4-Dichlorobenzoyl)-5-fluoro-3H-spiro[2-benzofuran-1,4'-piperidin]-3-one;
1'-(3,4-Dichlorobenzoyl)-6-(2-hydroxyethoxy)-3H-spiro[2-benzofuran-1,4'-piperidin]-3-one;
1'-(2,3-Dichlorobenzoyl)-3H-spiro[2-benzofuran-1,4'-piperidin]-3-one;
1'-(2,3-Dichlorobenzoyl)-6-methoxy-3H-spiro[2-benzofuran-1,4'-piperidin]-3-one;
6-Chloro-1'-(2,3-dichlorobenzoyl)-3H-spiro[2-benzofuran-1,4'-piperidin]-3-one;
1'-(2,3-Dichlorobenzoyl)-5-methoxy-3H-spiro[2-benzofuran-1,4'-piperidin]-3-one;
1'-(2,3-Dichlorobenzoyl)-5-fluoro-3H-spiro[2-benzofuran-1,4'-piperidin]-3-one;
1'-(2,3-Dichlorobenzoyl)-6-(2-hydroxyethoxy)-3H-spiro[2-benzofuran-1,4'-piperidin]-3-one;
1'-[(5-Chloro-1H-indazol-7-yl)carbonyl]-3H-spiro[2-benzofuran-1,4'-piperidin]-3-one;
1'-[(5-Chloro-1H-indazol-7-yl)carbonyl]-6-methoxy-3H-spiro[2-benzofuran-1,4'-piperidin]-3-one;
1'-(1-Naphthoyl)-3H-spiro[2-benzofuran-1,4'-piperidine];
4-Fluoro-1-(1-naphthoyl)-3H-spiro[2-benzofuran-1,4'-piperidine];
1'-(4-tert-Butylbenzoyl)-3H-spiro[2-benzofuran-1,4'-piperidine];
1'-[(2,2-Difluoro-1,3-benzodioxol-4-yl)carbonyl]-3H-spiro[2-benzofuran-1,4'-piperidine];
1'-(1H-Benzimidazol-7-ylcarbonyl)-3H-spiro[2-benzofuran-1,4'-piperidine];
1'-(1H-Indol-7-ylcarbonyl)-3H-spiro[2-benzofuran-1,4'-piperidine];
1'-(1,3-Benzodioxol-4-ylcarbonyl)-3H-spiro[2-benzofuran-1,4'-piperidine];
3,3-Dimethyl-6-(1'H,3H-spiro[2-benzofuran-1,4'-piperidin]-1'-ylcarbonyl)-1,3-dihydro-2H-indol-2-one; and
1'-(3,4-Dichlorobenzoyl)spiro[1-benzofuran-3,4'-piperidine].

25. The compound of claim 24, selected from the group consisting of
6-Methoxy-1'-(2-naphthoyl)-3H-spiro[2-benzofuran-1,4'-piperidin]-3-one,
1'-(3,4-Dichlorobenzoyl)-3H-spiro[2-benzofuran-1,4'-piperidin]-3-one,
1'-(3,4-Dichlorobenzoyl)-6-methoxy-3H-spiro[2-benzofuran-1,4'-piperidin]-3-one,
1'-(3,4-Dichlorobenzoyl)-5-methoxy-3H-spiro[2-benzofuran-1,4'-piperidin]-3-one,
1'-(3,4-Dichlorobenzoyl)-5-fluoro-3H-spiro[2-benzofuran-1,4'-piperidin]-3-one,
1'-(3,4-Dichlorobenzoyl)-6-(2-hydroxyethoxy)-3H-spiro[2-benzofuran-1,4'-piperidin]-3-one, and
1'-(4-tert-Butylbenzoyl)-3H-spiro[2-benzofuran-1,4'-piperidine].

26. A pharmaceutical composition comprising a therapeutically effective amount of a compound of formula I

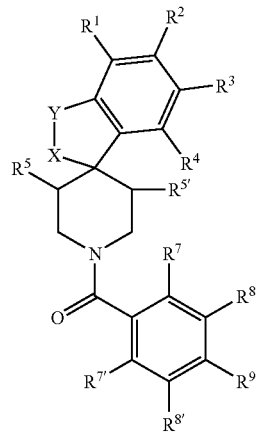

wherein
  X is O and Y is C=O,
  X is O and Y is $CH_2$,
  X is $CH_2$ and Y is O, or
  X is C=O and Y is O;
  $R^1$, $R^2$, $R^3$ and $R^4$ are each independently
    hydrogen,
    halo,
    $C_{1-6}$-alkyl, optionally substituted by OH,
    halo-$C_{1-6}$-alkyl,
    $C_{1-6}$-alkoxy, optionally substituted by OH, or
    halo-$C_{1-6}$-alkoxy;
  $R^5$ and $R^{5'}$ are each independently hydrogen or methyl;
  $R^7$, $R^{7'}$ $R^8$, $R^{8'}$, and $R^9$ are each independently selected from
    hydrogen,
    halo,
    $C_{1-6}$-alkyl,
    halo-$C_{1-6}$-alkoxy,
    nitro, and
    cyano,
  or $R^7$ and $R^8$, $R^{7'}$ and $R^{8'}$, $R^8$ and $R^9$, or $R^{8'}$ and $R^9$ are bound together to form a ring with the phenyl moiety,
    wherein
    —$R^7$—$R^8$— or —$R^{7'}$—$R^{8'}$— is
      —N($R^{10}$)—N=CH—, or —CH=N—N($R^{10}$)—,
        wherein $R^{10}$ is hydrogen or $C_{1-6}$-alkyl,
      —N($R^{11}$)—CH=CH—, or —CH=CH—N($R^{12}$)—,
        wherein $R^{11}$ is hydrogen or $C_{1-6}$-alkyl,
      —C($R^{12}$)=C($R^{13}$)—C($R^{14}$)=C($R^{15}$)—,
        wherein $R^{12}$, $R^{13}$, $R^{14}$, and $R^{15}$ are each independently selected from hydrogen, halo, halo-$C_{1-6}$-alkyl, $C_{1-6}$-alkyl, $C_{1-6}$-alkoxy, halo-$C_{1-6}$-alkoxy, nitro, and cyano,
      —O—($CR^{16}R^{16'}$)$_n$—O—,
        wherein n is 1 or 2, and $R^{16}$ and $R^{16'}$ are each independently hydrogen, halo or $C_{1-6}$-alkyl,
      —N($R^{17}$)—CH=N—, or —N=CH—N($R^{17}$)—,
        wherein $R^{17}$ is hydrogen or $C_{1-6}$-alkyl, or
      —N($R^{18}$)—C(O)—$CH_2$— or —$CH_2$—C(O)—N($R^{18}$)—,
        wherein $R^{18}$ is hydrogen or $C_{1-6}$-alkyl,
  or a pharmaceutically acceptable salt thereof and a pharmaceutically acceptable carrier.

* * * * *

UNITED STATES PATENT AND TRADEMARK OFFICE
CERTIFICATE OF CORRECTION

PATENT NO.       : 8,084,609 B2                                    Page 1 of 1
APPLICATION NO.  : 11/955452
DATED            : December 27, 2011
INVENTOR(S)      : Bissantz et al.

It is certified that error appears in the above-identified patent and that said Letters Patent is hereby corrected as shown below:

ON THE TITLE PAGE, Item (73)

-The Assignee information reads "Hoffman-La Roche Inc., Nutley, NJ (US)". The Assignee information should read -- Hoffmann-La Roche Inc., Nutley, NJ (US) --.

Signed and Sealed this
Fourteenth Day of February, 2012

David J. Kappos
*Director of the United States Patent and Trademark Office*